(12) United States Patent
Turnbull et al.

(10) Patent No.: US 9,889,150 B2
(45) Date of Patent: Feb. 13, 2018

(54) AGENTS FOR THE PREVENTION AND/OR TREATMENT OF CENTRAL NERVOUS SYSTEM DAMAGE

(71) Applicants: The University Of Liverpool, Liverpool (GB); The University Court of the University of Glasgow, Glasgow (GB)

(72) Inventors: Jeremy Ewan Turnbull, Liverpool (GB); Scott Ernest Guimond, Liverpool (GB); Sophie Marie Thompson, Liverpool (GB); Susan Carol Barnett, Glasgow (GB); Jennifer Rosemary Higginson, Glasgow (GB)

(73) Assignees: The University Of Liverpool (GB); The University Court of the University of Glasgow (GB)

( * ) Notice: Subject to any disclaimer, the term of this patent is extended or adjusted under 35 U.S.C. 154(b) by 0 days.

(21) Appl. No.: 14/440,005

(22) PCT Filed: Nov. 1, 2013

(86) PCT No.: PCT/GB2013/052863
§ 371 (c)(1),
(2) Date: Apr. 30, 2015

(87) PCT Pub. No.: WO2014/068327
PCT Pub. Date: May 8, 2014

(65) Prior Publication Data
US 2015/0272984 A1   Oct. 1, 2015

(30) Foreign Application Priority Data
Nov. 1, 2012 (GB) .................................. 1219696.0

(51) Int. Cl.
| | | |
|---|---|---|
| *A61K 31/727* | (2006.01) | |
| *A61K 39/39* | (2006.01) | |
| *C08B 37/10* | (2006.01) | |
| *A61K 39/395* | (2006.01) | |
| *A61K 38/46* | (2006.01) | |
| *A61K 38/51* | (2006.01) | |
| *C12N 15/113* | (2010.01) | |
| *A61K 35/30* | (2015.01) | |
| *C07K 16/22* | (2006.01) | |

(52) U.S. Cl.
CPC ............ *A61K 31/727* (2013.01); *A61K 35/30* (2013.01); *A61K 38/465* (2013.01); *A61K 38/51* (2013.01); *A61K 39/3955* (2013.01); *C07K 16/22* (2013.01); *C12N 15/1137* (2013.01); *C12Y 301/06011* (2013.01); *C12Y 301/06014* (2013.01); *C12Y 402/02007* (2013.01); *C07K 2317/76* (2013.01); *C12N 2310/14* (2013.01); *C12Y 402/02008* (2013.01)

(58) Field of Classification Search
CPC .............. A61K 31/727; C08B 37/0075; C08B 37/0078
See application file for complete search history.

(56) References Cited

U.S. PATENT DOCUMENTS

| | | | |
|---|---|---|---|
| 4,717,719 A | 1/1988 | Sportoletti et al. | |
| 5,296,471 A | 3/1994 | Holme et al. | |
| 6,489,311 B1 | 12/2002 | Kennedy | |
| 2009/0238852 A1 | 9/2009 | Kennedy et al. | |
| 2010/0062998 A1* | 3/2010 | Turnbull ............ | A61K 31/7016 514/54 |
| 2010/0266554 A1* | 10/2010 | Mori ...................... | A61K 35/28 424/93.7 |
| 2012/0101059 A1 | 4/2012 | Galesso et al. | |

FOREIGN PATENT DOCUMENTS

| | | |
|---|---|---|
| JP | 2005068057 A | 3/2005 |
| JP | 2005218308 A | 8/2005 |
| WO | 9625169 A2 | 8/1996 |
| WO | 0119376 A2 | 3/2001 |
| WO | 2009011892 A2 | 1/2009 |

OTHER PUBLICATIONS

Kapadia, M. et al "Autoimmune and inflammatory mechanisms of CNS damage" Prog. Neurobiol. (2011) vol. 95, pp. 301-333.*
Colangelo, A. et al "Astrogliosis as a therapeutic target . . . " Neurosci. Lett. (2014) vol. 565, pp. 59-64.*
Pekny, M. et al "Astrocyte reactivity and reactive astrogliosis . . . " Physiol. Rev. (2014) vol. 94, pp. 1077-1098.*
Monzon-Mayor, et al "Long-term evolution of local, proximal and remote astrocyte . . . " Brain Res. (2000) vol. 865, pp. 245-258.*
Huang, J. et al "Fibroblast growth factor 9 prevents MPP+-induced death . . . " J. Neurochem. (2009) vol. 109, pp. 1400-1412.*
Tada, T. et al "Fibroblast growth factor 1 is produced prior to apolipoprotein E . . . " Neurochem. Int. (2004) vol. 45, pp. 23-30.*
Polito V. A. et al: "Correction of CNS defects in the MPSII mouse model via systemic enzyme replacement herapy", Human Molecular Genetics, vol. 19, No. 24, Sep. 27, 2010 (Sep. 27, 2010), pp. 4871-4885, XP055098179, ISSN: 0964-6906, DOI: 10.1093/hmg/ddq420 abstract.
Pike C J et al: "Beta-amyloid-induced changes in cultured astrocytes parallel reactive astrocytosis associated with senile plaques in Alzheimer's disease.", Neuroscience Nov. 1994, vol. 63, No. 2, Nov. 1994 (Nov. 1994), pp. 517-531, XP055098550, ISSN: 0306-4522 abstract.
Kreuger J et al: "Characterization of fibroblast growth factor 1 binding heparan sulfate domain", Glycobiology, vol. 9, No. 7, Jul. 1999 (Jul. 1999), pp. 723-729, XP055098561, DOI: 10.1093/glycob/9.7.723 abstract p. 726, col. 2, paragraph 2—p. 727, col. 2, paragraph 3.

(Continued)

*Primary Examiner* — Leigh C Maier
(74) *Attorney, Agent, or Firm* — Lerner, David, Littenberg, Krumholz & Mentlik, LLP

(57) ABSTRACT

The present invention relates to the use of agents (including heparin derivatives) for the prevention and/or treatment of CNS damage.

13 Claims, 10 Drawing Sheets

(56) References Cited

OTHER PUBLICATIONS

Santos-Silva A. et al: "FGF/Heparin Differentially Regulates Schwann Cell and Olfactory Ensheathing Cell Interactions with Astrocytes: A Role in Astrocytosis", Journal of Neuroscience, vol. 27, No. 27, Jul. 4, 2007 (Jul. 4, 2007), pp. 7154-7167, XP055091135, ISSN: 0270-6474, DOI: 10.1523/JNEUROSCI. 1184-07.2007.

Fairless R et al: "N-cadherin differentially determines Schwann cell and olfactory ensheathing cell adhesion and migration responses upon contact with astrocytes", Molecular and Cellular Neurosciences, San Diego, US, vol. 28, No. 2, Feb. 2005 (Feb. 2005), pp. 253-263, XP004767077, ISSN: 1044-7431, DOI: 10.1016/J.MCN. 2004.09.009.

Zhang Dan et al: "Astrogllosis in CNS Pathologies: Is There a Role for Microglia?", Molecular Neurobiology, vol. 41, No. 2-3, Jun. 2010 (Jun. 2010), pp. 232-241, P055098607, ISSN: 0893-7648, DOI: 10.1007/s12035-010-8098-4 p. 232, col. 2, paragraph 1—p. 234, col. 1, paragraph 1.

UK Search Report for Application No. GB121696.0 dated Mar. 4, 2013.

International Search Report and Written Opinion for Application No. PCT/GB2013/052863 dated Apr. 28, 2014.

\* cited by examiner

|  | D1 | D2 | D3 | D4 | D5 | D6 | D7 | D8 |
|---|---|---|---|---|---|---|---|---|
|  | ΔUA-GlcNAc | ΔUA-GlcNAc(6S) | ΔUA-GlcNS | ΔUA-GlcNS(6S) | ΔUA(2S)-GlcNS | ΔUA(2S)-GlcNS(6S) | ΔUA(2S)-GlcNAc | ΔUA(2S)-GlcNAc(6S) |
| HEP1 | 6.8 | - | 3.4 | 13.4 | 7.0 | 67.4 | - | 2.0 |
| HEP2 | 14.2 | 7 | - | - | - | 3.5 | - | 75.3 |
| HEP3 | 7.1 | - | 13.7 | 79.2 | - | - | 0 | 0 |
| HEP4 | 15.5 | - | 43.2 | 7.0 | 34.3 | - | - | - |
| HEP5 | 14.4 | 62.9 | 3.4 | 19.3 | - | - | - | - |
| HEP6 | 55.8 | 7.7 | - | - | - | - | 34.8 | 1.7 |
| HEP7 | 19.1 | - | 79.1 | - | - | 1.8 | - | - |
| HEP8 | 99 | - | - | - | - | - | - | 1.0 |

Figure 10

AGENTS FOR THE PREVENTION AND/OR TREATMENT OF CENTRAL NERVOUS SYSTEM DAMAGE

CROSS-REFERENCE TO RELATED APPLICATIONS

The present application is a national phase entry under 35 U.S.C. § 371 of International Application No. PCT/GB2013/052863, filed Nov. 1, 2013, published in English, which claims priority from GB 1219696.0, filed Nov. 1, 2012, all of which are incorporated herein by reference.

FIELD OF THE INVENTION

The present invention relates to agents for use in the prevention and/or treatment of central nervous system damage. More specifically, the present invention relates to agents useful for promoting CNS repair by the prevention and/or treatment of reactive astrocytosis.

BACKGROUND OF THE INVENTION

Damage to the central nervous system (CNS), either following injury or disease, is largely permanent and irreversible, mainly due to the limited capacity of the CNS for repair. The ability to treat CNS damage and promote CNS repair therefore represents a major area of unmet clinical need.

A key pathological hallmark of CNS damage is a change in the phenotype of astrocytes[1]. Astrocytes are defined by their stellar morphology, and expression of the glial fibrillary acidic protein (GFAP). They play an active role in organising brain structure and function[2,3]. After injury or disease, the astrocyte phenotype alters and acquires a state referred to as reactive astrocytosis[3-5], in which it becomes enlarged, proliferates and changes shape. Numerous molecular pathways involving GFAP, vimentin and nestin as well as heparan sulphate proteoglycans (HSPGs), chondroitin sulphate proteoglycans and growth factors are altered[4,6] Reactive astrocytosis is the key player in the formation of a glial scar, which is one of the most dramatic responses following injury and significantly hampers CNS repair[3]. The scar isolates areas of tissue damage and excludes non neural cells from the CNS parenchyma resulting from injury[4]. The search for the initial molecular inducer of inhibitory reactive astrocytosis is ongoing, but clearly, manipulating the astrocyte response to injury could lead to successful therapeutic strategies to enhance repair of CNS tissue.

Injury to the mammalian CNS often leads to a series of secondary events including death of local neurons, degeneration of axons, loss of myelin sheaths, initiation of an immune response and the formation of the glial scar by reactive astrocytes (astrocytosis). Due to these dramatic cellular events, the injury site is walled off by a scar and damage to non-functional tissue is generated; this is most apparent in spinal cord injury (SCI)[7]. One strategy being developed for CNS repair is glial cell transplantation, in which damaged tissue is grafted with cells that naturally support axonal regeneration and/or myelination[7-9]. This is a particularly strong strategy for repair of spinal cord injury, in which transplanted cells not only participate in repair but also bridge the gap in the damaged tissue to encourage axons to cross the injury site[7-9]. Many cell types have been studied, including glial cells, in particular, olfactory ensheathing cells (OECs, supporting glia in the olfactory system) and Schwann cells (SCs, supporting nerve glial cells). Both of these glial cell types can play a significant role in promoting axonal outgrowth and myelination after transplantation into a traumatic lesion. However, despite this profuse ingrowth of axons within the lesion, regenerating axons cannot cross the scar boundary formed in the host tissue at the lesion site.

There are also some important differences between OECs and SCs that might influence their selection for transplantation. This difference, which has been detected not only in vitro[10,23], but also after transplantation in vivo, results in better integration of OECs than SCs with host astrocytes[11,33].

It has been shown that OECs and SCs share many biological characteristics, including antigenic and morphological phenotypes and the ability to myelinate axons with peripheral-type myelin[7,22,25,26]. However, they interact differently with astrocytes, the main component of the glial scar[24], in that SCs induce a reactive astrocyte phenotype, through which axons cannot regenerate[40,46], whereas OECs do not[10,11,23]. This is in line with the native behaviour of OECs in the olfactory system where they intermix with astrocytes[34,42]. Studies have demonstrated that SCs and astrocytes form a boundary on contact and occupy distinct, non-overlapping areas[10].

In contrast, OECs and astrocytes freely intermingle, without inducing a reactive astrocyte phenotype, although the addition of SC-conditioned medium (SCM) or heparin can induce SC-like behaviour in OECs. Furthermore, SCs will mingle with astrocytes if treated with an FGF receptor (FGFR) inhibitor, suggesting an involvement of heparan sulfate (HS)-dependent FGF signalling[11].

Therefore, overall, of the two glial cell types studied, OECs have become a preferred candidate for transplantation due to their ability to evoke less of an astrocyte stress response[10-12]. However, the repair capacity of OECs may also be compromised by secreted factors from endogenous SCs invading the injury site when the blood brain barrier has been compromised[13,14].

Accordingly, there is a need for improved approaches for promoting CNS repair in response to injury/damage.

There is also a need for improved approaches for preventing and/or treating reactive astrocytosis and glial scarring.

In addition, there is a need for improved glial transplantation strategies.

SUMMARY OF THE INVENTION

The present invention resides in the recognition that certain agents (as defined hereinafter) can act as inhibitors of reactive astrocytosis (and therefore glial scar formation). Accordingly, the agents defined herein are potentially useful for the treatment of CNS damage by inhibiting reactive astrocytosis responses and thereby promoting CNS repair. In addition to their use in the treatment of CNS damage, the agents of the present invention may also be used prophylactically to help prevent CNS damage during certain invasive procedures, for example surgery, or transplantation of cells.

The agents of the present invention can also be used in combination with glial cell transplantation, especially SC cell transplantation, to minimise the scar formation caused by reactive astrocytosis.

Thus, in a first aspect, the present invention provides an agent as defined herein, or a pharmaceutically acceptable salt or solvate thereof, for use in the prevention and/or treatment of CNS damage.

In a further aspect, the present invention provides a method of preventing and/or treating CNS damage, the method comprising administering to a subject in need of such treatment a therapeutically effective amount of an agent as defined herein, or a pharmaceutically acceptable salt or solvate thereof.

In a further aspect, the present invention provides the use of an agent as defined herein, or a pharmaceutically acceptable salt or solvate thereof, in the manufacture of a medicament for use in the prevention and/or treatment of CNS damage.

In another aspect, the present invention provides a pharmaceutical composition for use in the treatment of CNS damage comprising an agent as defined herein, or a pharmaceutically acceptable salt or solvate thereof, in admixture with a pharmaceutically acceptable diluent or carrier.

In a further aspect, the present invention provides an agent as defined herein, or a pharmaceutically acceptable salt or solvate thereof, for use in the prevention and/or treatment of CNS damage arising as a consequence of glial cell (e.g. SC) transplantation.

In a further aspect, the present invention provides a method of treating CNS damage, the method comprising transplanting glial cells into the site of injury of a subject in need of such treatment and administering a therapeutically effective amount of an agent as defined herein, or a pharmaceutically acceptable salt or solvate thereof.

In a further aspect, the present invention provides the use of an agent as defined herein, or a pharmaceutically acceptable salt or solvate thereof, in the manufacture of a medicament for use in the prevention and/or treatment of CNS damage arising as a consequence of glial cell (e.g. SC) transplantation.

In another aspect, the present invention provides a pharmaceutical composition for use in the treatment of CNS damage arising as a consequence of glial cell (e.g. SC) transplantation comprising an agent as defined herein, or a pharmaceutically acceptable salt or solvate thereof, in admixture with a pharmaceutically acceptable diluent or carrier.

Without wishing to be bound by any particular theory, it is believed that the agents of the present invention exert their therapeutic effects, at least in part, by inhibiting the activity of HS-dependent FGF signalling pathways.

Thus, in a further aspect, the present invention provides an agent as defined herein, or a pharmaceutically acceptable salt or solvate thereof, for use in the inhibition of HS-dependent FGF signalling.

In a further aspect, the present invention provides the use of an agent as defined herein, or a salt or solvate thereof, as an inhibitor of HS-dependent FGF signalling (in vitro or in vivo).

In a further aspect, the present invention provides a method of inhibiting the activity of HS-dependent FGF signalling (in vitro or in vivo), the method comprising administering an effective amount of an agent as defined herein, or a pharmaceutically acceptable salt or solvate thereof.

In yet another aspect, the present invention provides an agent which is obtainable by/obtained by/directly obtained by any one of the methods defined herein.

Further aspects of the invention are outlined in the following detailed description of the invention.

DETAILED DESCRIPTION OF THE INVENTION

Definitions

Unless otherwise stated, the following terms used in the specification and claims have the following meanings set out below.

It is to be appreciated that references to "preventing" or "prevention" relate to prophylactic treatment and includes preventing or delaying the appearance of clinical symptoms of the state, disorder or condition developing in a human that may be afflicted with or predisposed to the state, disorder or condition but does not yet experience or display clinical or subclinical symptoms of the state, disorder or condition.

It will be appreciated that references to "treatment" or "treating" of a state, disorder or condition includes: (1) inhibiting the state, disorder or condition, i.e., arresting, reducing or delaying the development of the disease or a relapse thereof (in case of maintenance treatment) or at least one clinical or subclinical symptom thereof, or (2) relieving or attenuating the disease, i.e. causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "alkyl" includes both straight and branched chain alkyl groups as well as cycloalkyl groups. References to individual alkyl groups such as "propyl" are specific for the straight chain version only and references to individual branched chain alkyl groups such as "isopropyl" are specific for the branched chain version only. For example, "(1-8C) alkyl" includes (1-4C)alkyl, (1-3C)alkyl, propyl, isopropyl, t-butyl, cyclohexyl, cyclopentyl, cyclobutyl and cyclopropyl. In a particular embodiment, an "alkyl" group is a (1-8C) alkyl group. In another embodiment, an "alkyl" group is a (1-6C)alkyl group.

A "substituted alkyl" group is an alkyl group bearing one or more substituent groups. In an embodiment, the substituent groups are selected from halo, amino, hydroxy, nitro, cyano, (1-6C)alkoxy, aryl, (2-6C)acyl, amido or phosphate groups.

The term "aryl" means a cyclic or polycyclic aromatic ring having from 6 to 12 carbon atoms. Examples of aryl groups include, but are not limited to, phenyl, biphenyl, naphthyl and the like. In particular embodiment, an aryl group is phenyl.

The term "substituted aryl" refers to aryl groups bearing one or more substituent groups. In an embodiment, the substituent groups are selected from halo, amino, hydroxy, nitro, cyano, (1-6C)alkyl, (1-6C)alkoxy, (2-6C)acyl, or amido groups.

The term "acyl" is used herein to refer to groups of the formula $R^a$—CO—, wherein $R^a$ is selected from (1-8C)alkyl or aryl. In an embodiment, an acyl group is (2-6C)acyl group, such as acetyl, pentanoyl or pivaloyl. In another embodiment, the acyl group is an aryl-acyl group, such as a benzoyl or phthaloyl group. In a preferred embodiment, the acyl group is acetyl.

The term "substituted acyl" is used herein to refer to an acyl group substituted with one or more suitable substituent groups. In an embodiment, an acyl group is substituted with one or more halo atoms, such a fluorine, chlorine or bromine. Particular examples of substituted acyl groups include mono-, di- or tri-fluoroacetyl groups.

The term "halo" refers to fluoro, chloro, bromo and iodo.

The term "amido" is used herein to refer to a group of the formula —CONH$_2$.

The term "substituted amido" is used herein to refer groups of the formula —CONR$^b$R$^c$ or —NR$^b$CO—R$^c$, wherein R$^b$ is hydrogen or (1-6C)alkyl and R$^c$ is selected from substituted or unsubstituted (1-6C)alkyl or substituted or unsubstituted aryl. Examples of substituted amido groups include methylamido, ethylamido or phthalamido groups.

Where substituents are chosen from "one or more" groups it is to be understood that this definition includes all substituents being chosen from one of the specified groups or the substituents being chosen from two or more of the specified groups.

Agents

The agents of the present invention may be selected from:
(i) modified heparin derivatives as defined herein;
(ii) enzyme therapies
(iii) selective FGF-1 or FGF-9 inhibitors;
(iv) other inhibitors of FGFR signalling pathways;

(i) Heparin Derivatives

Heparin is widely used clinically as an anticoagulant. The anticoagulant activity of heparin arises from it ability to increase the rate of formation of irreversible complexes between antithrombin III and the serine protease clotting factors X$_a$ and IIa. However, attenuation of the anticoagulant activity of heparin is vital if its derivatives are to be developed for use as pharmaceuticals for different therapeutic applications.

Unfractionated and low molecular weight heparins are highly sulphated glycosaminoglycan having a molecular weight typically ranging from 3 kDa to 30 kDa. It consists of 1,4 linked disaccharide repeat units of α-L-iduronic or β-D-glucuronic acid linked to either N-acetyl or N-sulpho-α-D-glucosamine. The principal positions of O-sulphation are C-2 of the uronate moieties and C-6 of the glucosamine moieties as well as, more rarely, C-3 of the glucosamine moiety. The most common disaccharide unit present in heparin is composed of a 2-O-sulphated iduronic acid and a 6-O-sulphated, N-sulphated glucosamine. However, variable substitution during biosynthesis does result in considerable sequence diversity.

The present invention relates to the use of particular heparin derivatives, as defined herein.

The heparin derivatives of the present invention are:
substantially 2-O desulphated and 2-N desulphated;
substantially 6-O desulphated and 2-N desulphated;
substantially 2-O and 6-O desulphated; or
substantially 2-O, 6-O and 2-N desulphated.

Therefore, the heparin derivatives of the present invention are comprised of one or more disaccharide units, each comprising a uronate moiety linked to a glucosamine moiety, wherein:

1. the 2-O atom of the uronate moiety is substantially desulphated and the 2-N atom of the glucosamine moiety is substantially desulphated;
2. the 6-O atom of the glucosamine moiety is substantially desulphated and the 2-N atom of the glucosamine moiety is substantially desulphated;
3. the 2-O atom of the uronate moiety is substantially desulphated and the 6-O atom of the glucosamine moiety is substantially desulphated;
4. the 2-O atom of the uronate moiety and the 6-O atom of the glucosamine moiety are substantially desulphated and the 2-N atom of the glucosamine moiety is substantially desulphated.

The heparin derivatives of the present invention advantageously possess little or no anticoagulant activity.

By "substantially 6-O desulphated", we mean that 10 to 100% of the 6-O atoms of the glucosamine moieties of the native heparin molecule are desulphated, i.e. the sulphate groups are replaced with hydrogen atoms.

In an embodiment, 30 to 100% of the 6-O atoms of the glucosamine moieties of the heparin molecule are desulphated, i.e. the sulphate groups are replaced with hydrogen atoms.

In a further embodiment, 50 to 100% of the 6-O atoms of the glucosamine moieties of the heparin molecule are desulphated, i.e. the sulphate groups are replaced with hydrogen atoms.

In a further embodiment, 75 to 100% of the 6-O atoms of the glucosamine moieties of the heparin molecule are desulphated, i.e. the sulphate groups are replaced with hydrogen atoms.

In a further embodiment, 90 to 100% of the 6-O atoms of the glucosamine moieties of the heparin molecule are desulphated, i.e. the sulphate groups are replaced with hydrogen atoms.

In a further embodiment, 90 to 95% of the 6-O atoms of the glucosamine moieties of the heparin molecule are desulphated, i.e. the sulphate groups are replaced with hydrogen atoms.

In a further embodiment, 95 to 100% of the 6-O atoms of the glucosamine moieties of the heparin molecule are desulphated, i.e. the sulphate groups are replaced with hydrogen atoms.

In certain embodiments, the heparin derivatives of the present invention are also substantially 2-O desulphated. By "substantially 2-O desulphated" we mean that 10 to 100% of the 2-O atoms on the uronate moieties of the native heparin molecule are desulphated, i.e. the sulphate groups are replaced with hydrogen atoms. In further embodiments, 30 to 100%, 50 to 100%, 75 to 100%, 90 to 100% or 90 to 95% of the 2-O atoms on the uronate moieties of the native heparin molecule are desulphated, i.e. the sulphate groups are replaced with hydrogen atoms.

In certain embodiments of the invention, the heparin derivatives of the present invention may be substantially 2-N-sulphated on the glucosamine moiety (e.g. greater than 70% or 75% sulphated).

In alternative embodiments of the invention, the heparin derivatives of the invention are substantially 2-N desulphated on the glucosamine moiety. Thus, in certain embodiments, the heparin derivatives of the present invention may comprise glucosamine residues that are substantially 2-N desulphated on the glucosamine in addition to having glucosamine moieties that are substantially 6-O desulphated and, optionally, uronate moieties that are substantially 2-O desulphated.

By "substantially 2-N desulphated", we mean that 10 to 100% of the 2-N atoms of the glucosamine moieties of the native heparin molecule are desulphated, i.e. the sulphate groups present on the 2-N atoms are replaced with hydrogen atoms or a substituent group as defined herein. In an embodiment, 30 to 100% of the 2-N atoms of the glucosamine moieties of the native heparin molecule are desulphated. In a further embodiment, 50 to 100% of the 2-N atoms of the glucosamine moieties of the native heparin molecule are desulphated. In yet another embodiment, 70 to 100%, 75 to 100%, 90 to 100%, 90 to 95% or 95 to 100% of the 2-N atoms of the glucosamine moieties of the native heparin molecule are desulphated.

Suitable substituents for the 2-N atom of the glucosamine moiety are any organic or inorganic chemical group other than sulphate ($SO_3$). In an embodiment, the 2-N atom of the glucosamine moieties are substituted with a substituent selected from the group consisting of hydrogen, substituted or unsubstituted alkyl, substituted or unsubstituted aryl, substituted or unsubstituted acyl, substituted or unsubstituted amido and phosphate.

The 2-N alkyl group may be linear, branched or cyclic and is preferably a (1-6C) alkyl group, optionally substituted with one or more atoms or groups, such as halogen atoms (e.g. fluorine, chlorine or bromine) or aryl, acyl, amido or phosphate groups. The amido group bonded directly to the 2-N glucosamine atom and/or the amido group bonded to the alkyl group bonded to the 2-N glucosamine atom may take any convenient form, such as a methylamido, ethylamido or phthalamido group. The substituted or unsubstituted acyl group bonded directly to the 2-N glucosamine atom and/or the acyl group bonded to the alkyl group bonded to the 2-N glucosamine atom may be linear (e.g. pentanoyl) or branched (e.g. pivaloyl) and is preferably a 1-6C substituted or unsubstituted acyl group. The acyl group may be an arylacyl group, such as a benzoyl group. The acyl group may be substituted with one or more halogen atoms, particularly fluorine, chlorine or bromine atoms. Preferred N-acyl groups are mono-, di- and tri-fluoroacetyl group. A further preferred N-acyl group is a phthaloyl group. Preferably the 2-N glucosamine atom is substituted with an acyl group selected from the group consisting of substituted or unsubstituted acetyl, substituted or unsubstituted proprionyl and substituted or unsubstituted butanoyl. Most preferably the glucosamine 2-N atom is substituted with an unsubstituted acetyl group.

In an embodiment of the invention, the heparin derivatives are substantially 2-O desulphated and substantially 2-N desulphated (e.g. 2-N substituted as defined hereinbefore). In such an embodiment, the level of 2-O and 2-N desulphation may be any of the levels defined previously herein. In a specific embodiment, the level of 2-O desulphation is 85 to 100% and the level of 2-N desulphation is 70 to 100%. In another embodiment, the level of 2-O desulphation is 90 to 100% and the level of 2-N desulphation is 90 to 100% or 95 to 100%. The level of 6-O sulphation in such embodiments may be, for example, between 70 to 100% or between 75 to 100%.

In a particular group of embodiments of the invention, the heparin derivatives are:
 (i) substantially 6-O desulphated and substantially 2-O desulphated as defined herein;
 (ii) substantially 6-O desulphated and substantially 2-N desulphated (e.g. 2-N substituted) as defined herein; or
 (iii) substantially 2-O desulphated, substantially 6-O desulphated, and substantially 2-N desulphated (e.g. 2-N substituted) as defined herein.

Thus, in an embodiment of the invention, the heparin derivatives are substantially 6-O desulphated and substantially 2-O desulphated as defined herein. In such an embodiment, the level of 6-O and 2-O desulphation may be any of the levels defined previously herein. In a specific embodiment, the level of 6-O desulphation is 85 to 100% and the level of 2-O desulphation is 70 to 100%. In another embodiment, the level of 6-O desulphation is 90 to 100%; the level of 2-O desulphation is 75 to 100%. The level of 2-N sulphation in such embodiments may be, for example, between 70 to 100% or between 75 to 100%.

In a further embodiment of the invention, the heparin derivatives are substantially 6-O desulphated and substantially 2-N desulphated (e.g. 2-N substituted as defined hereinbefore). In such an embodiment, the level of 6-O and 2-N desulphation may be any of the levels defined previously herein. In a specific embodiment, the level of 6-O desulphation is 85 to 100% and the level of 2-N desulphation is 70 to 100%. In another embodiment, the level of 6-O desulphation is 90 to 100% and the level of 2-N desulphation is 90 to 100% or 95 to 100%. The level of 2-O sulphation in such embodiments may be, for example, between 70 to 100% or between 75 to 100%.

In a further embodiment of the invention, the heparin derivatives are substantially 2-O, 6-O and 2-N desulphated (e.g. 2-N substituted) as defined herein. In such an embodiment, the level of 2-O, 6-O and 2-N desulphation may be independently any of the levels defined previously herein. In a specific embodiment, the level of 2-O and 6-O desulphation is 70 to 100% and the level 2-N desulphation is 90 to 100% or 95 to 100%. In another embodiment, the level of 2-O desulphation is 70 to 100%, the level of 6-O desulphation is 85 to 100% and the level of 2-N desulphation is 90 to 100% or 95 to 100%.

The average molecular weight of the heparin derivatives of the invention will range from 500 Da to 20 kDa. Suitably, the average molecular weight of the heparin derivatives of the invention will range from 500 Da to 15 kDa. In an embodiment, the average molecular weight of the heparin derivatives is from 2 kDa to 15 kDa. In a further embodiment, the average molecular weight of the heparin derivatives is from 10 kDa to 15 kDa.

The degree of polymerisation of the heparin derivatives of the present will range from 2 monomer units (i.e. a disaccharide) up to 60 monomer units.

In an embodiment, the degree of polymerisation of the heparin derivatives of the present will range from 4 monomer units up to 60 monomer units.

In a further embodiment, the degree of polymerisation of the heparin derivatives of the present will range from 10 monomer units up to 60 monomer units.

In an embodiment, the heparin derivatives of the invention will comprise a mixture of different size heparin derivatives. In such cases, the average degree of polymerisation of the heparin derivatives will range from 2 monomer units (i.e. a disaccharide) up to 60 monomer units, and more suitably 4-60 monomer units.

In an embodiment, the heparin derivatives of the present invention may be represented by the general structural formula I shown below:

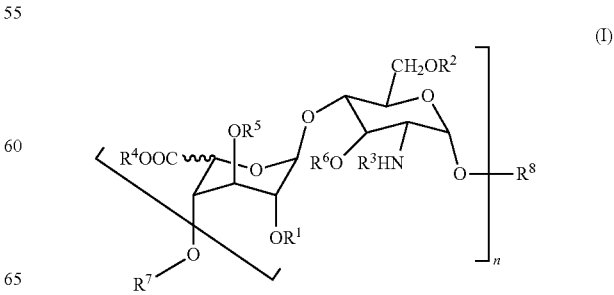

wherein:

$R^1$ and $R^2$ are selected from hydrogen or sulphate;

n is 1 to 30;

$R^3$ is selected from sulphate, hydrogen, substituted or unsubstituted alkyl, substituted or unsubstituted aryl, substituted or unsubstituted acyl, substituted or unsubstituted amido and phosphate;

$R^4$, $R^5$ and $R^6$ are each separately selected from the group consisting of hydrogen, sulphate, phosphate, substituted or unsubstituted (1-6C)alkyl, substituted or unsubstituted (1-6C)alkoxy, substituted or unsubstituted aryl, substituted or unsubstituted aryloxy, substituted or unsubstituted acyl, and substituted or unsubstituted amido; and $R^7$ and $R^8$ are each separately selected from the group consisting of hydrogen, substituted or unsubstituted alkyl, substituted or unsubstituted aryl, substituted or unsubstituted acyl, a terminal monosaccharide group, a terminal disaccharide group and/or fragments or derivatives thereof;

or a pharmaceutically acceptable salt or solvate thereof; with the proviso that (i) substantially all (e.g. >70%) of the $R^1$ groups present are hydrogen and substantially all (e.g. >70%) of the $R^3$ groups present are hydrogen or a substituent group other than sulphate;

(ii) substantially all (e.g. >70%) of the $R^2$ groups present are hydrogen and substantially all (e.g. >70%) of the $R^3$ groups present are hydrogen or a substituent group other than sulphate;

(iii) substantially all (e.g. >70%) of the $R^1$ and $R^2$ groups present are hydrogen; or (iv) substantially all (e.g. >70%) of the $R^1$ and $R^2$ groups present are hydrogen; and substantially all (e.g. >70%) of the $R^3$ groups present are hydrogen or a substituent group other than sulphate.

The bond shown as ∼∼∼ in formula I above is intended to show that the group —COOR$^4$ may be above (as in β-D) glucuronate moiety) or below (as in (α-L)iduronate moiety) the plane of the ring. It will be appreciated that the uronate moiety may also be a (α-L)galacturonate (although this is not shown).

In an embodiment, substantially all (e.g. >70%) of the $R^1$ groups present in the molecule are hydrogen, substantially all (e.g. >70%) of the $R^3$ groups present are hydrogen or a substituent group other than sulphate and substantially all (e.g. >70%) of the $R^2$ groups present in the molecule are sulphate.

In an embodiment, substantially all (e.g. >70%) of the $R^2$ groups present in the molecule are hydrogen, substantially all (e.g. >70%) of the $R^3$ groups present are hydrogen or a substituent group other than sulphate and substantially all (e.g. >70%) of the $R^1$ groups present in the molecule are sulphate.

In an embodiment, substantially all (e.g. >70%) of the $R^1$ and $R^2$ groups present in the molecule are hydrogen, and substantially all (e.g. >70%) of the $R^3$ groups present are sulphate;

In an embodiment, substantially all (e.g. >70%) of the $R^1$ and $R^2$ groups present in the molecule are hydrogen, and substantially all (e.g. >70%) of the $R^3$ groups present are hydrogen or a substituent group other than sulphate.

Particular heparin derivatives of this embodiment of the invention include, for example, compounds of Formula I, or pharmaceutically acceptable salts thereof, wherein, unless otherwise stated, each of $R^1$, $R^2$, $R^3$, $R^4$, $R^5$, $R^6$, $R^7$, and $R^8$ has any of the meanings defined hereinbefore or in any of paragraphs (1) to (55) hereinafter:—

(1) n is 1;
(2) n is 2 to 30;
(3) n is 2 to 20;
(4) n is 2 to 10;
(5) between 30-100% of all $R^2$ groups present are hydrogen;
(6) between 50-100% of all $R^2$ groups present are hydrogen;
(7) between 75-100% of all $R^2$ groups present are hydrogen;
(8) between 90-100% of all $R^2$ groups present are hydrogen;
(9) between 90-95% of all $R^2$ groups present are hydrogen;
(10) between 30-100% of all $R^2$ and $R^1$ groups present are hydrogen;
(11) between 50-100% of all $R^2$ and $R^1$ groups present are hydrogen;
(12) between 75-100% of all $R^2$ and $R^1$ groups present are hydrogen;
(13) between 90-100% of all $R^2$ and $R^1$ groups present are hydrogen;
(14) between 90-95% of all $R^2$ and $R^1$ groups present are hydrogen;
(15) between 30-100% of all $R^2$ groups present are hydrogen and 30-100% of the $R^3$ groups present are hydrogen or a substituent group other than sulphate as defined herein (e.g. acetyl);
(16) between 50-100% of all $R^2$ groups present are hydrogen and 50-100% of the $R^3$ groups present are hydrogen or a substituent group other than sulphate as defined herein (e.g. acetyl);
(17) between 75-100% of all $R^2$ groups present are hydrogen and 75-100% of the $R^3$ groups present are hydrogen or a substituent group other than sulphate as defined herein (e.g. acetyl);
(18) between 90-100% of all $R^2$ groups present are hydrogen and 90-100% of the $R^3$ groups present are hydrogen or a substituent group other than sulphate as defined herein (e.g. acetyl);
(19) between 90-95% of all $R^2$ groups present are hydrogen and 90-100% of the $R^3$ groups present are hydrogen or a substituent group other than sulphate as defined herein (e.g. acetyl);
(20) between 30-100% of all $R^2$ and $R^1$ groups present are hydrogen and 30-100% of the $R^3$ groups present are hydrogen or a substituent group other than sulphate as defined herein (e.g. acetyl);
(21) between 50-100% of all $R^2$ and $R^1$ groups present are hydrogen and 50-100% of the $R^3$ groups present are hydrogen or a substituent group other than sulphate as defined herein (e.g. acetyl);
(22) between 75-100% of all $R^2$ and $R^1$ groups present are hydrogen and 75-100% of the $R^3$ groups present are hydrogen or a substituent group other than sulphate as defined herein (e.g. acetyl);
(23) between 90-100% of all $R^2$ and $R^1$ groups present are hydrogen and 90-100% of the $R^3$ groups present are hydrogen or a substituent group other than sulphate as defined herein (e.g. acetyl);
(24) between 90-95% of all $R^2$ and $R^1$ groups present are hydrogen and 90-100% of the $R^3$ groups present are hydrogen or a substituent group other than sulphate as defined herein (e.g. acetyl);
(25) $R^3$ is sulphate;
(26) $R^3$ is hydrogen, substituted or unsubstituted (1-8C)alkyl, substituted or unsubstituted aryl, substituted or unsubstituted (2-8C)acyl, substituted or unsubstituted amido or phosphate;
(27) $R^3$ is hydrogen, unsubstituted (1-6C)alkyl, unsubstituted aryl, or unsubstituted (2-6C)acyl;
(28) $R^3$ is hydrogen, (1-4C)alkyl, phenyl, or acetyl;
(29) $R^3$ is hydrogen;

(30) $R^3$ is acetyl;
(31) between 10-100% of all $R^3$ groups present are hydrogen or a substituent group other than sulphate;
(32) between 30-100% of all $R^3$ groups present are hydrogen or a substituent group other than sulphate;
(33) between 50-100% of all $R^3$ groups present are hydrogen or a substituent group other than sulphate;
(34) between 70-100% of all $R^3$ groups present are hydrogen or a substituent group other than sulphate;
(35) between 75-100% of all $R^3$ groups present are hydrogen or a substituent group other than sulphate;
(36) between 90-100% of all $R^3$ groups present are hydrogen or a substituent group other than sulphate;
(37) between 95-100% of all $R^3$ groups present are hydrogen or a substituent group other than sulphate;
(38) $R^4$ is selected from the group consisting of hydrogen, substituted or unsubstituted (1-6C)alkyl, or substituted or unsubstituted aryl;
(39) $R^4$ is selected from the group consisting of hydrogen, unsubstituted (1-6C)alkyl, or unsubstituted aryl;
(40) $R^4$ is hydrogen or sulphate;
(41) $R^4$ is hydrogen;
(42) $R^5$ is selected from the group consisting of hydrogen, sulphate, phosphate, substituted or unsubstituted (1-6C)alkyl, substituted or unsubstituted (1-6C)alkoxy, substituted or unsubstituted aryl, substituted or unsubstituted aryloxy, substituted or unsubstituted acyl, and substituted or unsubstituted amido;
(43) $R^5$ is selected from the group consisting of hydrogen, sulphate, phosphate, unsubstituted (1-6C)alkyl, unsubstituted (1-6C)alkoxy, unsubstituted aryl, sunsubstituted aryloxy, unsubstituted (2-6C)acyl, and substituted or unsubstituted amido;
(44) $R^5$ is hydrogen or sulphate;
(45) $R^5$ is hydrogen;
(46) $R^6$ is selected from the group consisting of hydrogen, sulphate, phosphate, substituted or unsubstituted (1-6C)alkyl, substituted or unsubstituted (1-6C)alkoxy, substituted or unsubstituted aryl, substituted or unsubstituted aryloxy, substituted or unsubstituted acyl, and substituted or unsubstituted amido;
(47) $R^6$ is selected from the group consisting of hydrogen, sulphate, phosphate, unsubstituted (1-6C)alkyl, unsubstituted (1-6C)alkoxy, unsubstituted aryl, sunsubstituted aryloxy, unsubstituted (2-6C)acyl, and substituted or unsubstituted amido;
(48) $R^6$ is hydrogen or sulphate;
(49) $R^6$ is hydrogen;
(50) $R^6$ is sulphate;
(51) $R^7$ and $R^8$ are each separately selected from the group consisting of hydrogen, substituted or unsubstituted (1-6C)alkyl, substituted or unsubstituted aryl, substituted or unsubstituted (2-6C)acyl, a terminal monosaccharide group, or a terminal disaccharide group;
(52) $R^7$ and $R^8$ are each separately selected from the group consisting of hydrogen, unsubstituted (1-6C)alkyl, unsubstituted aryl, unsubstituted (2-6C)acyl, a terminal monosaccharide group, or a terminal disaccharide group;
(53) $R^7$ and $R^8$ are both hydrogen;
(54) one of $R^7$ and $R^8$ is a mono- or di-saccharide moiety and the other is hydrogen;
(55) both of $R^7$ and $R^8$ are mono- or di-saccharide moieties.

In a particular embodiment, $R^4$ and $R^5$ are both hydrogen. In a further embodiment, $R^4$, $R^5$ and $R^6$ are all hydrogen.

In a group of heparin derivatives of the invention:
(i) substantially all of the $R^2$ groups are hydrogen (i.e. the molecule is 6-O desulphated as defined hereinbefore) and substantially all of the $R^1$ groups present are hydrogen (i.e. the molecule is 2-O desulphated as defined hereinbefore);
(ii) substantially all of the $R^2$ groups are hydrogen (i.e. the molecule is 6-O desulphated as defined hereinbefore) and substantially all of the $R^3$ groups present are hydrogen or a substituent other than sulphate as defined above (i.e. the molecule is 2-N desulphated (e.g. 2-N substituted) as defined hereinbefore); or
(iii) substantially all of the $R^1$ and $R^2$ groups are hydrogen (i.e. the molecule is substantially 2-O and 6-O desulphated as defined herein) and substantially all of the $R^3$ groups present are hydrogen or a substituent other than sulphate as defined above (i.e. the molecule is 2-N desulphated (e.g. 2-N substituted) as defined hereinbefore).

Thus, in a particular embodiment, substantially all of the $R^1$ and $R^2$ groups are hydrogen (i.e. the molecule is substantially 2-O and 6-O desulphated as defined herein). In such an embodiment, the level of 2-O and 6-O desulphation may be any of the levels defined previously herein. In a specific embodiment, the level of 2-O and 6-O desulphation is 85 to 100% (i.e. 85 to 100% of the $R^1$ and $R^2$ groups are hydrogen). In another embodiment, the level of 2-O and 6-O desulphation is 90 to 100% (i.e. 90 to 100% of the $R^1$ and $R^2$ groups are hydrogen). The level of 2-N sulphation in such embodiments may be, for example, between 70 to 100% or between 75 to 100% (i.e. 70 to 100% or 75 to 100% of the $R^3$ groups are sulphate).

In a further embodiment of the invention, substantially all of the $R^2$ groups are hydrogen (i.e. the molecule is 6-O desulphated as defined hereinbefore) and substantially all of the $R^3$ groups present are hydrogen or a substituent other than sulphate as defined above (i.e. the molecule is 2-N desulphated (e.g. 2-N substituted) as defined hereinbefore). In such an embodiment, the level of 6-O and 2-N desulphation may be any of the levels defined previously herein. In a specific embodiment, the level of 6-O desulphation is 85 to 100% (i.e. 85 to 100% of the $R^2$ groups are hydrogen) and the level of 2-N desulphation is 70 to 100% (i.e. 70 to 100% of the $R^3$ groups are hydrogen or a substituent group other than sulphate as defined herein). In another embodiment, the level of 6-O desulphation is 90 to 100% (i.e. 90 to 100% of the $R^2$ groups are hydrogen) and the level of 2-N desulphation is 90 to 100 or 95 to 100% (i.e. 90 to 100% or 95 to 100% of the $R^3$ groups are hydrogen or a substituent group other than sulphate as defined herein). The level of 2-O sulphation in such embodiments may be, for example, between 70 to 100% or between 75 to 100% (i.e. 70 to 100% or 75 to 100% of the $R^1$ groups are sulphate and the remainder may be hydrogen).

In a further embodiment of the invention, substantially all of the $R^1$ and $R^2$ groups are hydrogen (i.e. the molecule is substantially 2-O and 6-O desulphated as defined herein) and substantially all of the $R^3$ groups present are hydrogen or a substituent other than sulphate as defined above (i.e. the molecule is 2-N desulphated (e.g. 2-N substituted) as defined hereinbefore). In such an embodiment, the level of 2-O, 6-O and 2-N desulphation may be independently any of the levels defined previously herein. In a specific embodiment, the level of 2-O and 6-O desulphation is 70 to 100% (i.e. 70 to 100% of the $R^1$ and $R^2$ groups are hydrogen) and the level 2-N desulphation is 90 to 100% or 95 to 100% (i.e. 90 to 100% or 95 to 100% of the $R^3$ groups are hydrogen or a substituent group other than sulphate as defined herein). In another embodiment, the level of 2-O desulphation is 70 to 100% (i.e. 70 to 100% of the $R^1$ groups are hydrogen), the level of 6-O desulphation is 85 to 100% (i.e. 85 to 100% of the $R^2$ groups are hydrogen) and the level of 2-N desulphation is 90 to 100% or 95 to 100% (i.e. 90 to 100% or 95 to 100% of the $R^3$ groups are hydrogen or a substituent group other than sulphate as defined herein).

It will also be appreciated that where the compound of the present invention consists solely of a saccharide unit of Formula (I) in which one of $R^7$ and $R^8$ is hydrogen and the other one of $R^7$ and $R^8$ is a terminal monosaccharide, the compound as a whole will consist of an odd number of monosaccharide units, whereas, if $R^7$ and $R^8$ are the same (i.e. $R^7$ and $R^8$ are both hydrogen, monosaccharides or disaccharides) then the compound will consist of an even number of monosaccharide units. Moreover, if one of $R^7$ and $R^8$ is a monosaccharide and the other of $R^7$ and $R^8$ is a disaccharide then the compound will consist of an odd number of monosaccharides. Thus, Formula (I) above, and the other structural formulae presented herein, are all intended to encompass compounds containing both odd and even numbers of monosaccharide units.

Where $R^7$ is a terminal monosaccharide group it is preferred that $R^7$ is a glucosamine moiety or derivative or fragment thereof. $R^7$ may take the same structure as the glucosamine moiety in Formula (I) in which $R^2$, $R^3$ and $R^4$ are as defined above.

Where $R^7$ is a terminal disaccharide group, $R^7$ suitably has the structure of the bracketed disaccharide repeating unit such that the non-reducing terminal monosaccharide has the same general structure as the uronate moiety in Formula (I), i.e. an (α-L)iduronate, (β-D)glucuronate or (α-L)galacturonate moiety in which $R^1$, $R^4$ and $R^5$ have any one of the definitions set out herein. The disaccharide unit $R^7$ may include derivatives of one or both of the monosaccharides forming part of the bracketed disaccharide repeating unit. The non-reducing terminal monosaccharide may be an (α-L) iduronate, (β-D)glucuronate or (α-L)galacturonate moiety incorporating a Δ4-5 unsaturated ring (i.e. a C-to-C double bond between carbons 4 and 5 in the ring). Such unsaturation arises, for example, when polysaccharide fragments forming the compound are made by digestion with a bacterial lyase enzyme or a chemical beta-elimination process (commonly used to fragment heparin).

Where $R^8$ is a terminal monosaccharide group, $R^8$ is preferably a uronate moiety or derivative or fragment thereof. $R^8$ preferably has the same general structure as the uronate moiety in Formula (I), i.e. an (α-L)iduronate, (β-D) glucuronate or (α-L)galacturonate moiety in which $R^1$, $R^4$ and $R^5$ are as defined above.

Where $R^8$ is a terminal disaccharide group, $R^8$ preferably has the same general structure to the bracketed disaccharide repeat of Formula (I) such that the reducing terminal monosaccharide, may have the same structure as the glucosamine moiety in Formula (I) in which $R^2$, $R^3$ and $R^4$ are as defined above. Disaccharide unit $R^8$ may include derivatives of one or both of the monosaccharides forming part of the bracketed disaccharide repeating unit. The reducing terminal monosaccharide may be 2,5-anhydro-mannitol, a 2,5-anhydromannose residue, a 1,6 anhydro (bicyclic) ring structure, or a mannosamine residue. Production of the compound may involve nitrous acid digestion, in which case the reducing terminal monosaccharide R7 is likely to be 2,5-anhydromannitol, which is normally chemically reduced to a 2,5-anhydromannose residue. Production of the compound using a chemical beta elimination process, in which case some reducing terminal residues can also be found as a 1,6 anhydro (bicyclic) structure, generally derived from 6-O-sulphated glucosamine residues. In addition, the chemical beta-elimination process can also cause epimerisation of glucosamine residues to form mannosamine residues.

Thus, in an embodiment, and in reference to Formula (I) above, the compound may be represented by one of the following three preferred structures (Formula (II), (III) and (IV)) in which all R groups and n are as defined above in relation to Formula (I), and the uronate moiety is represented generally as an (α-L)iduronate or (β-D)glucuronate moiety for convenience, but could be a (α-L)galacturonate moiety instead.

In Formula (II), $R^7$ is a terminal glucosamine moiety of the same general structure as that included in the bracketed disaccharide repeating unit.

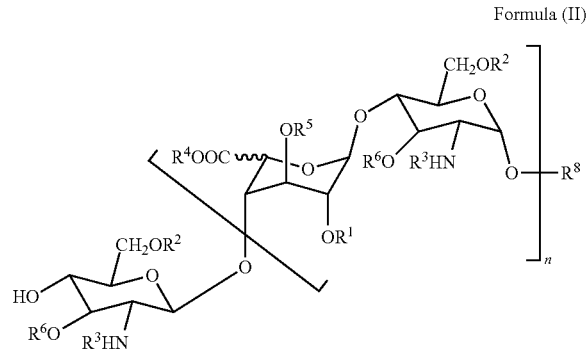

Formula (II)

In Formula (III), $R^8$ is a terminal uronate moiety of the same general structure as that included in the bracketed disaccharide repeating unit.

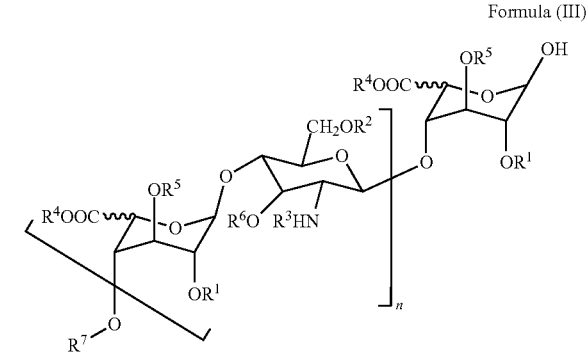

Formula (III)

In Formula (IV), $R^7$ is a terminal glucosamine moiety of the same general structure as that included in the bracketed disaccharide repeating unit and $R^8$ is a terminal uronate moiety of the same general structure as that included in the bracketed disaccharide repeating unit.

Formula (IV)

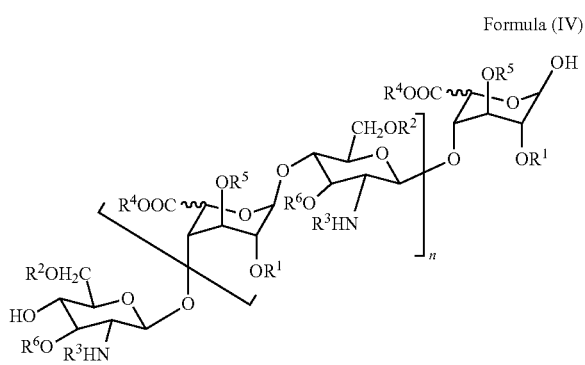

Particular heparin derivatives/compounds of the invention include the derivatives/compounds HEP6, HEP7 and HEP8 defined herein in the accompanying example section, or a pharmaceutically acceptable salt or solvate thereof.

Anticoagulant Activity

With regard to anti-coagulant activity, it is preferred that the heparin derivatives of the present invention exhibits less than around 20% of the Anti-Factor Xa activity of unmodified porcine intestinal mucosal heparin (PIMH). Preferably the heparin derivatives exhibits less than around 5%, more preferably less than around 1% of the Anti-Factor Xa activity of unmodified PIMH. It is particularly preferred that the heparin derivatives of the invention exhibits less than about 0.5%, still more preferably less than about 0.2% of the Anti-Factor Xa activity of unmodified PIMH.

Anti Factor Xa activity can be measured against a PIMH standard of known activity (Sigma, UK) using a diagnostic grade Coatest Heparin test kit (Chromogenix, MA), adapted to a 96-well plate format, reading A405 (Polarstar plate reader (BMG LabTechnologies, U.K.))[17].

Suitably, the heparin derivatives of the present invention show little or no Factor IIa activity, or little or no activity in Activated Partial Thromboplastin Time (APTT) and PT assays.

In reference to Example 3 herein, the exemplified heparin derivatives of the present invention show no detectable activity against Factor Xa and Factor IIa at concentrations that are 100 fold higher than the $IC_{50}$ of heparin. In addition, with the exception of the exemplified heparin derivatives D and D1, the exemplified heparin derivatives of the present invention also show no detectable inhibition at concentrations 100 fold higher than the $IC_{50}$ of heparin in the APTT assay described in Example 3. Furthermore, in the PT assay, the heparin derivatives of the present invention show no activity at 100 μg/ml.

A suitable pharmaceutically acceptable salt of a heparin derivative of the invention is, for example, an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It is also to be understood that the heparin derivatives of the invention may exist in solvated as well as unsolvated forms such as, for example, hydrated forms. It is to be understood that the invention encompasses all such solvated forms that possess the desired inhibition of astrocytosis and/or promotion of axon regeneration.

The in vivo effects of a heparin derivative of the invention may be exerted in part by one or more metabolites that are formed within the human or animal body after administration.

Preparation of Heparin Derivatives

The heparin derivatives of the present invention can be prepared from native heparin using techniques well known in the art.

The key chemical modifications required in order to produce the heparin derivatives of the present invention from native heparin include: the fragmentation of heparin molecules to produce derivatives of varying size fractions; chemical modification to remove sulphate groups at the 2-O position in the uronate moieties and/or the 6-O position of the glucosamine moieties; and chemical modification to provide N-sulphated or N-acylated glucosamine moieties.

Particular examples of techniques that may be utilised to form the heparin derivatives of the present invention from native heparin include:

(i) selective removal of 2-O sulphate from the uronate moieties;

(ii) selective removal of 6-O sulphate from the glucosamine moieties;

(iii) complete removal of O- and N-sulphates;

(iv) selective removal of N-sulphates;

(v) addition of N-sulphates (re-N-sulphation); and (vi) acylation of N groups (or re-N-acylation).

All of the above reactions can be carried out by techniques known in the art. Suitable examples of such techniques are described further in, for example, WO 2007/138263 and Patey et al., J. Med. Chem. 2006, 49, 6129-6132, the entire contents of which are incorporated herein by reference.

By way of example, reaction (i) above, i.e. the selective removal of 2-O sulphate groups from the uronate moieties, can be carried out by the techniques described in Jaseja et al. [Can. J. Chem. 1989, 67, 1449-1456]. Reaction (ii) above, i.e. the selective removal of 6-O sulphate from the glucosamine moieties, can be carried out by the techniques described in Inoue et al. [Anal. Biochem. 1975, 65, 164-174]. Reaction (iii) above, i.e. the complete removal of O- and N-sulphates, can be carried out by the techniques described in Inoue et al. [Anal. Biochem. 1975, 65, 164-174]. Reaction (iv) above, i.e. the selective removal of N-sulphates, can be carried out by employing solvolytic de-sulphation under kinetic control, as described by Inoue et al. [Carbohydr. Res. 1976, 46, 87-95]. Reaction (v) above, i.e. the addition of N-sulphates (re-N-sulphation), can be carried out by the use of trimethylamine-sulfur trioxide using the methodology described in Lloyd et al. [Biochem. Pharmacol. 1971, 20, 637-648]. Lastly, reaction (vi) above, i.e. acylation of N groups (or re-N-acylation), can be achieved using the techniques described in Yates et al. [Carbohydr. Res. 1996, 294, 15-27].

An example of a suitable native heparin source to use as a starting material is PIMH.

It will also be appreciated that the heparin derivatives described herein can also be produced by other methods. Synthetic chemistry approaches have been described for production of such derivatives, such as the heparin pentasaccharide Arixtra [U.S. Pat. No. 4,818,816; Angew. Chem. Int. Ed. 2004, 43, 3118] and also other heparin and HS structures [J. Am. Chem. Soc. 2009, 128, 2766-2767; J Am Chem Soc. 2006, 131, 17394-405; Chemistry. 2010, 26, 8365-75; Cole C L et al. PloS One 2010, 53-7; Nature Chemistry 2011, 3, 557-563]. Enzymatic and chemoenzymatic approaches have also been described using purified or recombinant enzymes involved in the natural biosynthesis of heparin/HS to modify oligosaccharide or polysaccharide substrates produced from bacterial fermentation or synthetic chemistry [*J. Biol. Chem.* 2005, 280, 42817; *Chem. Biol.* 2007, 14, 986; *J. Am. Chem. Soc.* 2008, 130, 12998; *J. Med. Chem.* 2005, 48, 349; *J. Biol. Chem.* 2010, 285, 34240; *Nat. Biotechnol.* 2003, 21, 1343].

In the preparation of the heparin derivatives of the invention, all proposed reaction conditions, including choice of solvent, reaction atmosphere, reaction temperature, duration of the experiment and workup procedures etc., can be selected by a person skilled in the art.

It is understood by one skilled in the art that the functionality present on various portions of the molecule must be compatible with the reagents and reaction conditions utilised.

(ii) Selective FGF-1 or FGF-9 Inhibitors

Compounds that are able to selectively inhibit the activity of FGF-1 and/or FGF-9 represent suitable agents in accordance with certain embodiments of the invention. In suitable embodiments selective FGF-1 or FGF-9 inhibitors of this sort may include compounds that are able to inhibit activity of these growth factors by inhibiting their expression. Examples of such compounds include antisense oligonucleotides, siRNA, and aptamers capable of binding to nucleic acid molecules encoding FGF-1 or FGF-9. Suitable examples of such agents may be designed or selected with reference to the sequences of the genes or mRNA encoding these growth factors, which are publicly available to those skilled in the art.

Alternatively, compounds that are able to selectively inhibit the activity of FGF-1 and/or FGF-9 may included compounds that are capable of neutralising the activity of these growth factors once expressed. Merely by way of example, such compounds may include small molecular agents, neutralising antibodies or aptamers capable of binding to FGF-1 and/or FGF-9 and thereby inhibiting the ability of these growth factors to induce the intracellular signalling necessary to achieve their biological activity. Suitable agents may, for example, inhibit the binding of these growth factors to their cognate receptors.

Inhibitors of FGFR Signalling Pathways

Other inhibitors of FGF-FGFR signalling pathways are also examples of agents of the present invention. These include compounds that are able to inhibit signalling pathways associated with receptors that bind FGF-1 and/or FGF-9, such as FGFR3-IIIb.

Examples of suitable inhibitors include small molecule agents that target the classical downstream pathways, for example:

MAP Kinase inhibitors (eg. PD98059, Sigma; UO126 Selleck) which block MEK activation;

AKT inhibitors (eg. API-59CJ-OMe, Calbiochem; Akt-I, Sigma);

PI3K inhibitors using pan inhibitors (e.g. GSK1059615, pan PI3K inhibitor, Selleck; Wortmanin, Sigma) and agents that act as inhibitors of specific isoforms (e.g. IC-87114 an PI3kδ isoform selective inhibitor, TGX-221 for PI3Kβ, Selleck).

PKC inhibitors (e.g. calphostin C, chelethryine chloride or staurosporine).

It will be appreciated that compounds able to specifically inhibit signalling associated with FGFR3-IIIb are likely to be of particular utility as agents of the invention. These include small molecule inhibitors that specifically reduce FGFR3-IIIb signalling in response to binding of this receptor to its ligands. Other examples of such compounds include soluble fragments of the FGFR3-IIIb that are able to bind to FGF-1 and/or FGF-9 without giving rise to intracellular signalling necessary for these growth factors to exert their biological activities. Alternative examples of such inhibitors include compounds that are able to bind to FGFR3-IIIb and thereby render it incapable of binding to FGF-1 and/or FGF-9. Examples of such inhibitors include neutralising antibodies directed to the FGFR3-IIIb. A still further group of such inhibitors include compounds that are capable of inhibit activity of this receptor by inhibiting its expression. Examples of such compounds include antisense oligonucleotides, siRNA, and aptamers capable of binding to nucleic acid molecules encoding the FGFR3-IIIb. Suitable examples of such agents may be designed or selected with reference to the sequences of the genes or mRNA encoding this receptor, which are publicly available to those skilled in the art.

Enzyme Therapies

Enzymes or compounds capable of increasing the expression or activity of such enzymes are also agents of the present invention. Such enzymes may be provided at the site where it is desired that they will exert their activity, through either administration of the selected enzyme itself, or administration of an agent capable of increasing the expression or activity of the selected enzyme.

The heparinases (a family of bacterial lyase enzymes that selectively degrade HS/heparin) are an example of such enzymes. Heparinase 1 cleaves highly sulphated domains, while a mixture of heparinases 1, 2 and 3 cleaves HS chains entirely. Heparinases, whether 1, 2, 3, or a mixture thereof, may be provided in an amount sufficient to modify and reduce the amount of HS produced by SCs, or other cells, either transplanted or at the site of injury. In a suitable embodiment heparinases may be provided in the form of exogenous enzyme.

Additionally or alternatively, Sulf 1 and/or Sulf 2 constitute suitable mammalian enzymes that may be provided as agents of the invention. Sulf 1 and Sulf 2 are sulfatases which selectively remove 6-O-suphate from HS. Sulf 1 and/or Sulf 2 may be provided in an amount sufficient to reduce HS sulfation levels. In a suitable embodiment Sulf 1 and/or Sulf 2 may be provided in the form of exogenous enzyme.

In an alternative embodiment, Sulf 1 and/or Sulf 2 may be provided via suitable agents encoding these enzymes. In suitable embodiment, such an agent may comprise a lentivirus that carries the sulf1 and/or sulf2 genes. Such a lentiviral vector may be used to infect SCs, or other transplanted cells, or other cells in the region to which the vector is provided, such that the infected cells express the Sulf1 and/or Sulf2 in an amount sufficient to reduce 6-O-sulphation, and thereby prevent and/or treat central nervous system damage.

Pharmaceutical Compositions

A further aspect of the present invention provides a pharmaceutical composition for use in the prevention and/or treatment of CNS damage which comprises an agent as defined hereinbefore, or a pharmaceutically acceptable salt or solvate thereof, in combination with a pharmaceutically acceptable carrier, diluent or excipient.

The compositions of the invention are suitably formulated for parenteral administration (for example as a sterile aqueous or oily solution for intracerebral or intraspinal dosing directly to the site of injury). In some cases, however, it might be appropriate to formulate the agent for administration by intravenous, intramuscular, sub-cutaneous, or intra-peritoneal injection or infusion.

The compositions of the invention may be obtained by conventional procedures using conventional pharmaceutical excipients, well known in the art. Thus, compositions intended for parenteral use may contain, for example, a suitable vehicle and, optionally, one or more preservative agents.

In some cases, the agent may be formulated for oral delivery, nasal, rectal or vaginal routes.

It will be appreciated that a suitable vehicle used for the agents of the invention should be one which is well tolerated by the subject to whom it is given and enables delivery of the agent to the desired site of action.

In one embodiment, the amount of the agent of the invention in a pharmaceutical composition of the invention is an amount from about 0.01 mg to about 800 mg. In another embodiment, the amount of the agent is an amount from about 0.01 mg to about 500 mg. In another embodiment, the amount of the agent is an amount from about 0.01 mg to about 250 mg. In another embodiment, the amount of the agent is an amount from about 0.1 mg to about 60 mg. In another embodiment, the amount of the agent is an amount from about 1 mg to about 20 mg.

Routes of Administration and Dosage

The agents of the invention may be administered in a number of ways depending on the desired site of action.

Suitably, the agent will be administered by injection. Depending on the nature of the agent, injections may be, for example, intracerebral, intracerebroventricular, intraspinal, intravenous, intra-arterial, intradermal, subcutaneous, intraperitoneal, or intrathecal. Such injections may be continuous over a period of time (infusion) or bolus injections.

In some cases, the agents may also be administered by inhalation (e.g. intranasally), orally, transdermally or by the rectal or vaginal routes.

The agents of the invention may also be incorporated into a slow or delayed release formulation or device. Such formulations or devices may, for example, be inserted on or under the skin and the heparin derivative may be released over weeks or even months.

It will be appreciated that the amount of the agents of the invention required is determined by biological activity and bioavailability which in turn depends on the mode of administration, the physicochemical properties of the derivative employed and whether the derivative is being used as a monotherapy or in a combined therapy. The frequency of administration will also be influenced by the above mentioned factors and particularly the half-life of the derivative within the subject being treated.

Optimal dosages of the agent to be administered may be determined by those skilled in the art, and will vary with the particular derivative being used, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the agent as well as precise dosage regimens.

Generally, a daily dose of between 0.01 µg/kg of body weight and 1.0 g/kg of body weight of the agent may be used for the treatment of CNS injury, depending upon which specific derivative is used. More preferably, the daily dose is between 0.01 mg/kg of body weight and 100 mg/kg of body weight.

Daily doses may be given as a single administration (e.g. as a single daily injection or infusion). Alternatively, the agent used may require administration two or more times during a day.

Therapeutic Uses and Applications

Therapeutic Uses

As previously described, the agents defined herein are potentially useful for the treatment of CNS damage by inhibiting reactive astrocytosis responses and thereby promoting CNS repair. In addition to their use in the treatment of CNS damage, the agents of the present invention may also be used prophylactically to help prevent CNS damage during certain invasive procedures, for example surgery, or transplantation of cells.

Thus, the agents of the present invention are useful for the prevention and/or treatment of CNS damage.

More specifically, the present invention agents as defined therein for use in the treatment and/or prevention of reactive astrocytosis.

As reactive astrocytosis is implicated in glial scar formation, the present invention further provides an agent as defined herein for use in the treatment of glial scar formation.

In light of the activity of the agents of the present invention, they are particularly suited for the treatment of CNS damage, which may result from injury, disease or as a consequence of certain medical or surgical procedures.

The agents of the present invention are also particularly suited to minimising reactive astrocytosis arising as a consequence of cell transplantation.

Reactive astrocytosis is particularly associated with SC transplantation, but the repair capacity of OECs may also be compromised by secreted factors from endogenous SCs invading the injury site when the blood brain barrier has been compromised[13,14]. Accordingly, in procedures involving the transplantation of SCs, OECs or any other cells (eg stem cells) that may beneficial for the promotion of CNS repair, it may be advantageous to either:

pre-treat the transplantation site with an agent as defined hereinbefore;

pre-treat the transplant cells with an agent as defined hereinbefore; and/or co-administer the transplant cells with an agent as defined hereinbefore.

continued administration for a period after repair or transplantation treatment is initiated Accordingly, the agents of the present invention are promising agents for use in the treatment and/or prevention of CNS damage, either alone or as a component of cell transplantation therapies.

Mechanism of Action

Studies on the mechanisms underlying the distinct interactions of SCs and OECs with astrocytes and the induction of reactive astrocytosis and boundary formation have shown that the mechanisms are differentially regulated by N-cadherin[12], are sensitive to FGFR inhibition and are dependent upon the structure of HS[11].

The mechanisms of action of the agents of the present invention are illustrated diagrammatically in FIG. 9.

Without wishing to be bound by any particular theory, it is believed that the agents of the present invention will exert their therapeutic effects, at least in part, by inhibiting the activity of HS-dependent FGF signalling pathways.

Thus, in a further aspect, the present invention provides an agent as defined herein, or a pharmaceutically acceptable salt or solvate thereof, for use in the inhibition of HS-dependent FGF signalling.

In a further aspect, the present invention provides the use of an agent as defined herein, or a salt or solvate thereof, as an inhibitor of HS-dependent FGF signalling (in vitro or in vivo).

In a further aspect, the present invention provides a method of inhibiting the activity of HS-dependent FGF signalling (in vitro or in vivo), the method comprising administering an effective amount of an agent as defined herein, or a pharmaceutically acceptable salt or solvate thereof.

The heparin derivatives of the present invention are believed to act as HS mimetics, which are postulated to decrease the activation of FGFR, particularly FGFR3-IIIb receptors, present on astrocytes. The binding of FGF to FGFR3-IIIb is understood to be mediated by highly sulphated HS, whereas the lower sulphated analogues of the present invention seem to inhibit this interaction and thereby prevent the phenotypic change in the astrocytes that results in reactive astrocytosis.

It is also believed that selective FGF-1 or FGF-9 inhibitors will serve to inhibit the stimulation of FGFRs present on astrocytes and thereby result in a reduction in reactive astrocytosis.

Inhibitors that act directly at the FGFRs, particularly FGF3-IIIb receptors, present on astrocytes will also block the activation of the phenotypic change in the astrocytes that results in reactive astrocytosis.

The enzyme therapies described herein also serve to reduce the amount of highly sulphated HS present at the site of injury/transplantation, thereby inhibiting the activation of FGFRs present on the astrocytes and the phenotypic change in the astrocytes that results in reactive astrocytosis.

Combination Therapies

The agents defined hereinbefore may be applied as a sole therapy or may involve, in addition to the agent of the invention, treatment with one or more additional therapeutic agents.

Such conjoint treatment may be achieved by way of the simultaneous, sequential or separate dosing of the individual components of the treatment. Such combination products employ the agents of this invention within the dosage range described hereinbefore and the other pharmaceutically-active agent within its approved dosage range.

According to this aspect of the invention there is provided a combination suitable for use in the treatment or prevention of CNS damage comprising an agent of the invention as defined hereinbefore, or a pharmaceutically acceptable salt thereof, and another therapeutic agent.

In a further aspect of the invention there is provided an agent of the invention or a pharmaceutically acceptable salt thereof, for use in the treatment of CNS damage, wherein the agent is administered in combination with another agent that promotes CNS repair/axon regeneration.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises an agent of the invention, or a pharmaceutically acceptable salt thereof, in combination with another therapeutic agent.

BRIEF DESCRIPTION OF THE FIGURES

FIG. 10. Table showing the disaccharide composition of the heparin derivatives prepared in Example 1.

EXAMPLES

Figure 1:
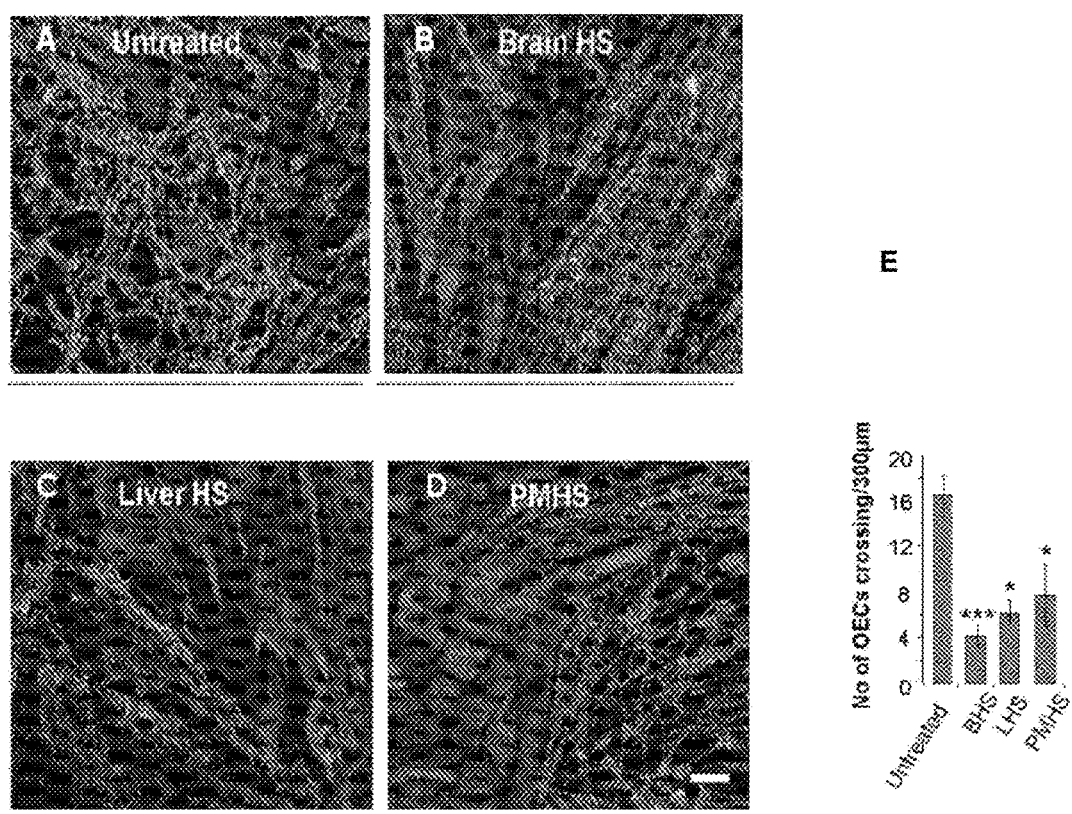
FIG. 1. HS from a variety of tissue sources can induce a boundary in OEC:astrocyte confrontation assays. 30 µg/ml HS purified from brain (BHS, B), liver (LHS, C) and porcine intestinal mucosa (PMHS, D), were added to confrontation assays of OECs and astrocytes and compared to an untreated control (A). After 2 days of treatment, cells were fixed and stained for GFAP (red) and $p75_{NTR}$ (green). The numbers of OECs mingling with astrocytes across a 300 µm line were counted (E). HS from all 3 tissue sources prevented OECs from crossing into the astrocyte monolayer, resulting in the formation of a boundary. Error bars indicate ±SEM. Scale bar 50 m. * $p<0.05$, *** $p<0.001$ versus control.

The invention will now be illustrated in the following Examples.

Example 1

Preparation of Modified Heparin Derivatives

Chemically modified heparin compounds (A) to (I) were prepared by the following combinations of reactions (a) to (g) set out below:

HEP1 PIMH starting material (Celsus Labs, Cincinnati, Ohio);

HEP2 N-acetyl heparin (d) (f);

HEP3 Ido 2-de-O-sulphated heparin (a);

HEP4 6-O-desulphated heparin (b) (e);

HEP5 Ido 2-de-O-sulphated, N-acetylated heparin (a) (d) (f);

HEP6 6-O-desulphated, N-acetylated heparin (b) (f);

HEP7 6-O-desulphated, 2-O-desulphated heparin (c) (e);

HEP8 6-O-desulphated, 2-O-desulphated, N-acetylated heparin (c) (f); and

HEP9 Per-sulphated heparin (g) (e).

Compounds were characterized by $^1$H and $^{13}$C NMR as previously described. (Yates et al., *Carbohydrate Research* 1996, 294, 15-27.) Compounds were desalted, lyophilized and re-suspended in the appropriate buffer prior to assay.

Chemical Reactions (a) Selective removal of iduronate 2-O-sulphate was achieved as described by Jaseja and Perlin. (Jaseja, M.; Rej, R. N.; Sauriol, F.; Perlin, A. S. *Can. J. Chem.* 1989, 67, 1449-1456.) Note that there is concomitant modification in the small number of N- and 3-O-sulphated glucosamine units. (Santini, F.; Bisio, A.; Guerrini, M.; Yates, E. A. *Carbohydrate Research* 1997, 302, 103-108.)

(b) Selective removal of glucosamine 6-O-sulphate was carried out according to a modification (Yates, E. A. et al. supra.) of the method described. (Inoue, S.; Miyawaki, M. *Analytical Biochemistry* 1975, 65, 164-174.)

(c) Complete removal of O- and N-sulphates was achieved using solvolytic de-sulphation by the method described. (Inoue, S.; Miyawaki, M. supra.)

(d) Selective de-N-sulphation was carried out employing controlled solvolytic de-sulphation under kinetic control as described. (Inoue, Y.; Nagasawa, K. *Carbohydrate Research* 1976, 46, 87-95.)

(e) Re N-sulphation was achieved by use of trimethylamine.sulfur trioxide complex as described. (Lloyd, A. G.; Embery, G.; Fowler, L. *J. Biochemical Pharmacology* 1971, 20, 637-648.)

(f) Re N-acetylation employed acetic anhydride in saturated sodium bicarbonate. (Yates, E. A. et al. supra.)

(g) Complete O-sulphation of all available hydroxyl groups was carried out using excess sulfur trioxide pyridine complex on the tetrabutylammonium salt of heparin in pyridine as described (Yates, E. A.; Santini, F.; De Cristofano, B.; Payre, N.; Cosentino, C. et al. *Carbohydrate Research* 2000, 329, 239-247.) followed by re-N-sulphation (Lloyd, A. G. et al. supra.) taking precautions to avoid formation of an unusual N-sulfoaziridine modification. (Yates, E. A.; Santini, F.; Bisio, A.; Cosentino, C. *Carbohydrate Research* 1997, 298, 335-340).

Compound Purity

The starting material for all chemical modifications was PIMH (Celsus Labs, Cincinnati, Ohio, USA; lot PH-42800 with anticoagulant activity 201 IU/mg).

Each polysaccharide HEP1-8 was subjected to purification by size-exclusion chromatography (Sephadex G-25, recovering only the exclusion limit; $M_w$>5 KDa) and treated with ion exchange resin (Dowex, W-50, $Na^+$ form) prior to NMR and activity testing.

Size-exclusion chromatography analysis of the 8 polysaccharides was also conducted with a TSK gel G2000SW$_{XL}$ column (7.8 mm×30 cm with 0.5 µm particle size; Supelco) eluting with water at 1 ml/min and detecting at 190 nm. All the samples exhibited a single major peak, with very similar retention times (mean, 6.07 minutes; $\sigma_{n-1}$=0.05). In all cases, there were no contaminants greater than 5%.

Polysaccharides HEP1-8 were also exhaustively digested with a mixture of heparinases I, II and III to their constituent disaccharides (here denoted D1 to D8) determined. Disaccharides were separated by strong-anion exchange HPLC (Propac PA-1 column, Dionex UK; [ref 2]) and quantified ($A_{232}$) with reference to authentic standards (Dextra Labs, Reading, UK) and showed the following composition (%). In all cases, unidentified peaks were <5% of the total area of the constituents. The data is shown in FIG. 10 and conforms exactly to the compositions predicted from the modifications performed, and are in agreement with the NMR structure data (see below).

NMR Spectroscopy

The polysascharides were characterised by $^1H$ and $^{13}C$ NMR to confirm their structure [Yates, E. A.; Santini, F.; Bisio, A.; Cosentino, C. *Carbohydrate Research* 1997, 298, 335-340]. NMR spectra were recorded in $D_2O$ at 40° C. on a 400 MHz instrument. Assignment was by a combination of COSY, TOCSY, HMBC two-dimensional spectra. $^{13}C$ spectra were recorded on 150 mg samples of the polysaccharide. Chemical shift values were recorded relative to trimethylsilyl propionate as reference standard at 40° C.

Table of $^1H$ and $^{13}C$ NMR chemical shift values for heparin derived polysaccharides HEP1-9

| Polysaccharide | Glucosamine | | | | | | Iduronate | | | | |
|---|---|---|---|---|---|---|---|---|---|---|---|
| | A-1 | A-2 | A-3 | A-4 | A-5 | A-6 | I-1 | I-2 | I-3 | I-4 | I-5 |
| HEP1 | 99.5 | 60.7 | 72.5 | 78.8 | 72.0 | 69.2 | 102.1 | 78.9 | 72.1 | 79.0 | 72.3 |
| | 5.42 | 3.31 | 3.69 | 3.79 | 4.05 | 4.30-4.42 | 5.23 | 4.37 | 4.22 | 4.14 | 4.82 |
| HEP2 | 96.6 | 56.2 | 73.0 | 79.3 | 72.3 | 69.6 | 102.2 | 76.8 | 67.3 | 74.2 | 70.8 |
| | 5.15 | 4.03 | 3.76 | 3.78 | 4.04 | 4.31-4.37 | 5.20 | 4.37 | 4.31 | 4.08 | 4.91 |
| HEP3 | 98.1 | 60.3 | 72.4 | 80.1 | 71.5 | 68.7 | 104.6 | 71.1 | 70.4 | 77.2 | 71.2 |
| | 5.34 | 3.24 | 3.65 | 3.71 | 4.02 | 4.36 4.23 | 5.04 | 3.78 | 4.12 | 4.08 | 4.84 |
| HEP4 | 100.0 | 60.8 | 72.4 | 80.5 | 73.8 | 62.6 | 102.0 | 77.6 | 70.7 | 78.7 | 71.4 |
| | 5.31 | 3.27 | 3.71 | 3.70 | 3.89 | 3.86-3.88 | 5.26 | 4.35 | 4.25 | 4.06 | 4.84 |
| HEP5 | 97.1 | 56.2 | 72.5 | 79.6 | 71.8 | 68.8 | 104.6 | 72.0 | 71.4 | 77.0 | 71.9 |
| | 5.18 | 4.00 | 3.78 | 3.79 | 4.08 | 4.37-4.26 | 5.01 | 3.75 | 3.42 | 4.10 | 4.78 |
| HEP6 | 96.8 | 56.6 | 72.9 | 80.6 | 74.2 | 62.9 | 102.3 | 76.6 | 67.1 | 74.1 | 70.6 |
| | 5.14 | 4.03 | 3.79 | 3.76 | 3.91 | 3.87-3.92 | 5.26 | 4.37 | 4.28 | 4.07 | 4.91 |
| HEP7 | 98.2 | 60.5 | 72.5 | 80.2 | 73.5 | 62.4 | 104.3 | 72.2 | 71.5 | 77.8 | 72.2 |
| | 5.39 | 3.26 | 3.67 | 3.72 | 3.87 | 3.84-3.88 | 4.95 | 3.74 | 4.11 | 4.08 | 4.77 |
| HEP8 | 97.1 | 56.2 | 72.3 | 79.6 | 73.7 | 62.3 | 104.3 | 72.5 | 72.2 | 77.3 | 72.6 |
| | 5.18 | 3.97 | 3.76 | 3.74 | 3.89 | 3.85-3.88 | 4.92 | 3.69 | 3.89 | 4.07 | 4.73 |
| HEP9 | 99.6 | 59.3 | 82.9 | 76.8 | 72.1 | 68.7 | 100.8 | 73.6 | 72.9 | 73.3 | 69.8 |
| | 5.32 | 3.50 | 4.48 | 4.04 | 4.05 | 4.27-4.41 | 5.32 | 4.55 | 4.72 | 4.39 | 5.05 |

The $^1H$ chemical shift values quoted for position-6 of glucosamine residues (A-6) are intervals. Signals from the carbonyl group of iduronate and acetyl $CH_3$ groups of N-acetylated glucosamine derivatives are not shown.

Example 2

The Anticoagulant Activity of the Heparin Derivatives Prepared in Example 1

Experimental Protocol:

The anti-factor Xa activity was measured against a PIMH standard of known activity using a diagnostic grade Coatest Heparin test kit (Chromogenix, MA), adapted to a 96-well plate format, reading A405.

Results:

The Table below shows the anticoagulant activity (anti-Xa activity) of the heparin derivatives described in Example 1 herein. Seven of the heparin-derivatives (HEP 2 to H) including the six O-de-sulphated heparins of the present invention (HEP to HEP8) show <1.5% anti-Xa activity compared with that of the standard heparin (HEP1).

Anticoagulant Activity Data[16]

| Compound | | $R_1$ | $R_2$ | $R_3$ | Anti-coagulant activity |
|---|---|---|---|---|---|
| HEP1 | PMIH | $SO_3$ | $SO_3$ | $SO_3$ | 100% |
| HEP2 | N-acetyl | $SO_3$ | $SO_3$ | $COCH_3$ | 0.03% |
| HEP3 | UA-2-OH | H | $SO_3$ | $SO_3$ | 0.4% |
| HEP4 | GlcN-6-OH | $SO_3$ | H | $SO_3$ | 0.5% |
| HEP5 | UA-2-OH, N-Acetyl | H | $SO_3$ | $COCH_3$ | 0.03% |
| HEP6 | GlcN-6-OH, N-acetyl | $SO_3$ | H | $COCH_3$ | 0.03% |
| HEP7 | UA-2-OH, GlcN-6-OH | H | H | $SO_3$ | 0.03% |
| HEP8 | UA-2-OH, GlcN-6-OH, N-acetyl | H | H | $COCH_3$ | 0.03% |
| HEP9 | Per-sulphated | $SO_3$ | $SO_3$ | $SO_3$ | 35.0% |

Example 3

Assessments of Anti-Coagulant Activity of the Heparin Derivatives

Factor Xa and Factor II activity was measured using a colorimetric substrate assay as previously described[17]. Briefly, in a 96 well ELISA plate, antithrombin III (American Diagnostica, 30 mIU/ml final concentration) was incubated with heparin or polysaccharide fractions in 0.9% NaCl at 37° C. for 2 minutes. Factor IIa (Sigma, 15 mU/ml final concentration) or Factor Xa (Thermo Scientific, 15 mU/ml final concentration) was added and the samples incubated for a further 1 minute at 37° C. Factor Xa Chromogenic substrate (Sigma, 240 uM final concentration) was added to the samples and incubated for 10 minutes at 37° C. The reaction was stopped with glacial acetic acid (Sigma, 25% final concentration). Colour change of the substrate was measured at 405 nm.

APTT and PT assays were performed using a Axis Shield Thrombotrack 1 instrument using normal human plasma, Pathrombin SL reagent and Thromborel S (all from Axis Shield) reagents according to manufacturers instructions.

For all assays, heparins and polysaccharides were tested up to 100 ug/ml. Heparin was an anticoagulant in all assays with IC50 values of 0.9, 1.0, 1.2 and 41.4 ug/ml for the Factor Xa, Factor II, APTT and PT assays respectively.

Results and Conclusion:

No polysaccharide fraction had anticoagulant activity (<1% of heparin activity).

Table Showing Anticoagulant Activity of Heparin and HEP5-8

| Compound | Structure | IC50 Factor Xa | IC50 Factor IIa | IC50 APTT | IC50 PT |
|---|---|---|---|---|---|
| Heparin | | 0.9295 | 1.0326 | 1.2461 | 41.4005 |
| Hep5 | I2OH, NAc | NI | NI | NI | NI |
| Hep6 | A6OH, NAc | NI | NI | NI | NI |
| Hep7 | I2OH, A6OH | NI | NI | NI | NI |
| Hep8 | I2OH, A6OH, NAc | NI | NI | NI | NI |

IC50s in ug/ml
NI: No inhibition of coagulation up to 100 ug/ml of compound

Example 4

Biological Evaluation

Materials and Methods
Generation of Purified Glial Cells

All primary neural cultures were generated from Sprague-Dawley rat pups of either sex. As described previously[10,37], purified type 1 astrocytes were prepared by digesting cortices (dissected from 1-day old Sprague Dawley (SD) rats) in 1.33% (w/v) collagenase (Sigma-Aldrich, Gillingham, UK), seeding (~2×10⁷ cells per 75 cm² flask) and culturing the cells in poly-L-lysine (PLL, 13.3 µg/ml, Sigma-Aldrich, Gillingham, UK) coated 75 cm2 flasks for 10-12 days. The cells were maintained in DMEM (Invitrogen, Paisley, Scotland) supplemented with 10% (v/v) foetal bovine serum (FBS) (Sigma-Aldrich, Gillingham, UK) and L-glutamine (2 mM, Sigma-Aldrich, Gillingham, UK) (DMEM-FBS). Confluent flasks were shaken on a rotary platform overnight at 37° C. to remove contaminating oligodendrocyte precursor cells. The remaining cells were 85-95% type 1 astrocytes as identified by labelling for glial fibrillary acidic protein (GFAP), an astrocyte cell specific marker.

OECs were isolated from the olfactory bulb of 7 day old SD rat pups and purified using magnetic nanoparticles (STEMCELL Technologies, UK) pre-bound with the $p75^{NTR}$ antibody (mouse IgG1, Abcam, Cambridge, UK)[30]. The cells were grown in low glucose DMEM with 5% (v/v) FBS and 2 mM L-glutamine and further supplemented with DMEM-BS (Bottenstein, 1979), FGF2 (25 ng/ml, Peprotech, London UK), heregulin β-1 (50 ng/ml, R&D Systems, Oxon, UK), forskolin (5×10-7 M Sigma-Aldrich, Gillingham, UK) and astrocyte conditioned media (ACM) (1:5, fresh serum-free media taken after incubation with a confluent astrocyte monolayer for 48 h)[18, 37].

SCs were purified using a modification of the method described by Brockes and colleagues[20]. This modification involved treating the cultures with cytosine arabinoside (AraC, $10^{-5}$ M, Sigma-Aldrich, Gillingham, UK), followed by incubation with anti-Thy1.1 antibody (1:1 supernatant, Sigma-Aldrich, Gillingham, UK) and rabbit complement (1:6, Harlan Laboratories Ltd., UK) to reduce contamination by fibroblasts[10]. All cell cultures were grown in PLL coated tissue culture flasks.

Collection of SC Conditioned Medium (SCM), OEC Conditioned Medium (OCM) and Astrocyte Conditioned Medium (ACM)

Confluent cultures of purified SCs or OECs in 75 cm2 flasks (maintained in vitro for 2-6 weeks) were rinsed twice with phosphate buffered saline (PBS), pH 7.4 and 7 ml of DMEM-BS without growth factors added. Cultures were maintained for a further 2 days before medium collection. Collected medium was centrifuged to remove cellular debris and filtered through a 0.2 µm filter (Millipore, Hertfordshire, UK). The same procedure was used for generating ACM, except that confluent astrocyte cultures were maintained in 11 ml of DMEM-BS. Conditioned media was added to cell cultures at a 1:1 ratio with DMEM-FBS.

Confrontation Assays

Confrontation assays were performed as described by Wilby et al. (1999) and Lakatos et al. (2000) with some modifications[10,48]. Briefly, 70 µl containing 10,000 OECs or SCs were seeded into one well of a silicon Ibidi culture insert on a PLL-coated glass coverslip (Ibidi GmbH, Munich, Germany). Into the opposing, parallel well, 10,000 astrocytes were seeded. Cells were allowed to attach for 1 h before careful removal of the insert followed by a wash with DMEM-FBS to remove unattached cells. Cultures were maintained in DMEM-FBS and allowed to grow towards each other over a period of 5-7 days, allowing time for cells to make contact and interact[10]. In some experiments, modified heparins or blocking antibodies were added to the cultures after the cells had contacted each other. Cultures were then immunolabelled using anti-GFAP for astrocytes (1:500; anti-rabbit (Dako, Ely, UK)) and anti-$p75_{NTR}$ for OECs and SCs (1:1; IgG1; hybridoma supernatant[49]. Fluorescent images were captured using an Olympus BX51 fluorescent microscope and Image-Pro software. Using Adobe Photoshop Elements 7.0, a 300 µm line was drawn along the interface between astrocytes and either OECs or SCs. The numbers of OECs or SCs crossing the cell:cell boundary were counted and averaged over five randomly chosen fields. Experiments were repeated at least three times.

Treatments:
Modified Heparins

Modified heparins were produced semisynthetically by chemical modification (selective desulfation) of heparin as described in Example 1. These structurally distinct, model "HS-mimetic" polysaccharides[50] are useful tools for investigating structure-activity relationships of HS[15-17,31]. Heparins were added to confrontation assays at 10 μg/ml at the stage when cells made contact (day 0) and treatment was repeated on day 2. Cultures were fixed and stained as described above on day 3.

HS from Various Tissue Sources

Porcine mucosal HS (PMHS) was a gift from Organon (Oss, Netherlands), porcine liver and rat brain HS were purified using previously described methods (Lyon and Gallagher, 1991; Esko, 2001). Confrontation assays were treated with polysaccharides for 2 days (day 0 and day 2) at a final concentration of 30 μg/ml.

Heparinase and Trypsin Treatment of Conditioned Medium

Proteins in SCM were digested by the addition of trypsin at a final ratio of 1:50 trypsin:protein and incubated for 12 h at 37° C. (amount of protein was estimated by measuring the UV absorbance at 280 nm). Trypsin was inactivated by addition of soybean trypsin inhibitor (1/10 of final trypsin concentration). HS was digested by the addition of 10 mU each of heparinase I (EC 4.2.2.7), II (EC number not assigned) and III (EC 4.2.2.8) (Ibex Technologies, Montreal, Canada) to 4 ml SCM, followed by incubation at 37° C. for 6 h. A further 10 mU of each heparinase enzyme was added to SCM and the reaction incubated overnight at 37° C. Treatment of confrontation assays was carried out by replacing half of the media with untreated SCM, heparinase-treated SCM, trypsin-treated SCM or 50:50 heparinase: trypsin treated SCM. Confrontation assays were treated for 2 days.

FGF Inhibition

Anti-FGF2 (Clone bFM-1) (Millipore, Hertfordshire, UK), anti-FGF9 (Clone 36912) and anti-FGF1 (both R&D Systems, Oxon, UK) neutralising antibodies were added to confrontation assays at a final concentration of 1 μg/mL, at the stage when cells made contact. Treatment was repeated for 2 days and then cultures were fixed and stained as described above on day 3.

HPLC Analysis of HS Disaccharides in SCM and OCM

SCM and OCM were collected from 75 cm2 flasks of confluent OECs or SCs, frozen and stored at −20° C. until enough material was collected for detection (180 mL OCM and 90 mL SCM). OCM and SCM were rotated with 0.1 ml DEAE-sephacel (Sigma-Aldrich, Gillingham, UK) per 10 mL, overnight at 4° C., and then centrifuged at 3382×g for 5 min and unbound material in the supernatant removed. DEAE beads were washed three times with 10 column volumes of PBS, and then washed twice with 10 column volumes of 0.25 M NaCl in PBS. Bound material containing HS proteoglycans (HSPGs) was eluted with 10 column volumes of 2 M NaCl in PBS and desalted over two, in-line 5 mL Hi Trap desalting columns (GE Healthcare UK Ltd, Buckinghamshire, UK) using an AKTA-FPLC system. Desalted material was then freeze-dried.

Heparinase Digestion

Lyophilised material was taken up in heparinase buffer (100 mM sodium acetate, 0.1 mM calcium acetate, pH 7) and 2.5 mU each of heparinase I, II and III were added and incubated for 3 h at 37|C. After this time, a further 2.5 mU of heparinase I, II and III were added and the reaction incubated overnight at 37|C. Another 2.5 mU of heparinase I, II and III were then added and incubated for a further 3 h. As a control, 100 μg heparin was digested in the same way. Digested samples were then incubated at 95° C. for 5 min to stop the reaction and taken up in 800 μl HPLC-grade water.

C18 HPLC

HS disaccharides were separated out from samples using a Discovery® C18 HPLC column (Supelco, Sigma-Aldrich, Gillingham, UK) (25 cm×4.6 mm, 5 μm) on a Simadzu SPD 10 A HPLC system. Buffer A was HPLC-grade water and Buffer B was 80% (v/v) methanol. Elution profiles were monitored by UV absorbance at 232 nm. Samples were injected in buffer A and the void volume containing HS disaccharides was collected and freeze-dried for BODIPY labelling. Bound material (containing hydrophobic material, including HSPG core proteins), was eluted using a linear gradient of 0-50% buffer B over 30 min at a flow rate of 1 ml min$^{-1}$.

BODIPY Labelling of HS Disaccharides

Freeze-dried HS disaccharides were labelled with BODIPY FL hydrazide (5 mg/ml; 4,4-di fluoro-5,7-di methyl-4-bora-3a,4a-diaza-s-indacene-3-propionic acid hydrazide; Molecular Probes) as previously described[52-54]. Digested heparin control and HS disaccharide standards (Iduron, Manchester, UK) were labelled in the same way. Labelled samples were applied to silica gel thin layer chromatography (TLC) aluminium plates and free BODIPY tag separated from labelled disaccharides with butanol. Labelled HS disaccharides were removed from the TLC plates and solubilised in 800 μl HPLC-grade water.

SAX-HPLC

SAX separations were performed on a Propac PA1 column (25 cm×9 mm, 5 μm) using a Simadzu SPD 10A HPLC system. Elution profiles were monitored by UV absorbance at 232 nm and fluorescent detection using a Shimadzu RF10AXL spectrofluorometer. Buffer A was 150 mM NaOH and Buffer B was 150 mM NaOH, 2 M NaCl. Elution profiles were monitored by UV absorbance at 232 nm and fluorescent detection at $\lambda_{ex}$=488 nm $\lambda_{em}$=520 nm. Samples were injected and the flow held at 2 ml min$^{-1}$ in buffer A until all remaining free tag had been eluted. Fluorescently labelled disaccharides were then eluted using a linear gradient of 0-50% buffer B over 45 min at 2 ml min$^{-1}$. The column was then washed with a 10 min elution in 300 mM NaOH, 2 M NaCl, before returning to 150 mM NaOH.

Quantitative Real-Time PCR

RNA from monocultures of OECs and SCs was extracted using a Qiagen RNeasy Mini Kit (Qiagen, West Sussex, UK) following manufacturer's instructions and RNA quality and integrity were checked using the Nanodrop 1000 (Thermo Fisher Scientific Inc, IL, USA). Following RNA extraction, cDNA was synthesised from 1 g RNA using the Quantitect Reverse Transcription kit (Qiagen, West Sussex, UK). Real-time PCR was performed with 100 ng cDNA in a 20 1 reaction volume using QuantiTect primer assays and the Quantifast SYBRgreen PCR kit (Qiagen, West Sussex, UK). Experiments were performed in triplicate for each sample in 96-well plates using the Applied Biosystems 7500 real-time PCR system. PCR cycle settings were 95° C. for 5 min, followed by 40 cycles of 95° C. for 10 s, then 60° C. for 30 s. Cycle threshold was calculated based on GAPDH (endogenous control), which was confirmed to be comparable in both cell types. Expression of all genes were expressed relative to GAPDH in each sample, derived using the comparative delta delta threshold change method (relative quantification, RQ). Three independent cell preparations were analysed.

Quantitative Real-Time PCR

RNA from monocultures of OECs and SCs was extracted using a Qiagen RNeasy Mini Kit (Qiagen, West Sussex, UK) following manufacturer's instructions and RNA quality and integrity were checked using the Nanodrop 1000 (Thermo Fisher Scientific Inc, IL, USA). Following RNA extraction, cDNA was synthesised from 1 µg RNA using the Quantitect Reverse Transcription kit (Qiagen, West Sussex, UK). Real-time PCR was performed with 100 ng cDNA in a 20 µl reaction volume using QuantiTect primer assays and the Quantifast SYBRgreen PCR kit (Qiagen, West Sussex, UK). Experiments were performed in triplicate for each sample in 96-well plates using the Applied Biosystems 7500 real-time PCR system. PCR cycle settings were 95° C. for 5 min, followed by 40 cycles of 95° C. for 10 s, then 60° C. for 30 s. Cycle threshold was calculated based on GAPDH (endogenous control), which was confirmed to be comparable in both cell types. Expression of all genes were expressed relative to GAPDH in each sample, derived using the comparative delta delta threshold change method (relative quantification, RQ). Three independent cell preparations were analysed.

siRNA Transfections

Purified OECs were seeded at a density of 5000 cells/100 µl into one chamber of an Ibidi culture insert (Ibidi GmbH, Munich, Germany) sealed onto a PLL coated coverslip in a well of a 24-well plate. Cells were cultured in defined OEC medium for 24 h, after which, the medium was replaced with low serum (2% (v/v) FBS) OEC medium containing 1 µM siRNA. siRNA sequences were obtained from Dharmacon/Thermo Scientific (Sulf 1: E-093746-00-0005; Sulf2: E-093673-00-0005; non-targeting: D-001910-01-05; Thermo Fisher Scientific Inc, IL, USA). Sulf 1 and Sulf 2 siRNAs were added in combination. After 72 h, astrocytes were seeded into the opposing chamber of the culture insert and confrontation assays performed as previously described. The extent of gene knockdown was assessed by qPCR using RNA purified from siRNA treated cells and Sulf 1 and Sulf 2 specific primers.

Results

The induction of astrocyte hypertrophy by SCs and the resulting formation of a cellular boundary remains a barrier to their use in cell transplantation therapies for the repair of spinal cord injury. Previous work has shown that SC induced boundary formation involves HS and FGFRs, since digestion of HS or chemical blockage of FGFR inhibits boundary formation and promotes cell mingling[11]. Improved knowledge of the biological factors and signalling pathways underlying SC-induced boundary formation will aid the development of strategies to improve the incorporation of transplanted SCs into host CNS tissue and prevent activation of an astrocytic stress response by invading host SCs, to facilitate injury repair.

HS from Different Sources Induces OEC/Astrocyte Boundaries

Heparin has been shown to induce a boundary between OECs and astrocytes[11]. To determine if this activating effect of heparin on boundary formation could be induced by more physiologically relevant HS species, confrontation assays of OECs and astrocytes were treated with HS purified from different tissues. Whilst OECs and astrocytes mingled freely in control assays (FIG. 1A), strong boundaries were formed upon addition of HS purified from rat brain (FIG. 1B), rat liver (FIG. 1C) or porcine intestinal mucosa (FIG. 1D). Quantification of the extent of boundary formation, assessed by the number of OECs crossing into the astrocyte monolayer, showed that HS from all 3 sources had similar activity (FIG. 1E).

Induction of an OEC/Astrocyte Boundary by SCM Requires Both a Protein and HS Component Initially, the relative requirements for protein and HS components in SCM for boundary formation were investigated. The active role of SCM HS in the induction of an OEC:astrocyte boundary was confirmed, since heparinase treatment of SCM negates the boundary forming effect (FIG. 2C). SCM treated separately with either heparinase or trypsin did not induce boundary formation (FIG. 2C, D, F), whilst combining the separately treated SCM samples reconstituted its biological activity and induced boundary formation (FIG. 2E, F). These data demonstrate that the activity of SCM in inducing boundary formation between cells requires both an HS and protein component, and that individually, these components are insufficient to induce a boundary.

HS Sulfation Determines the Induction of OEC/Astrocyte Boundaries

Figure 3:
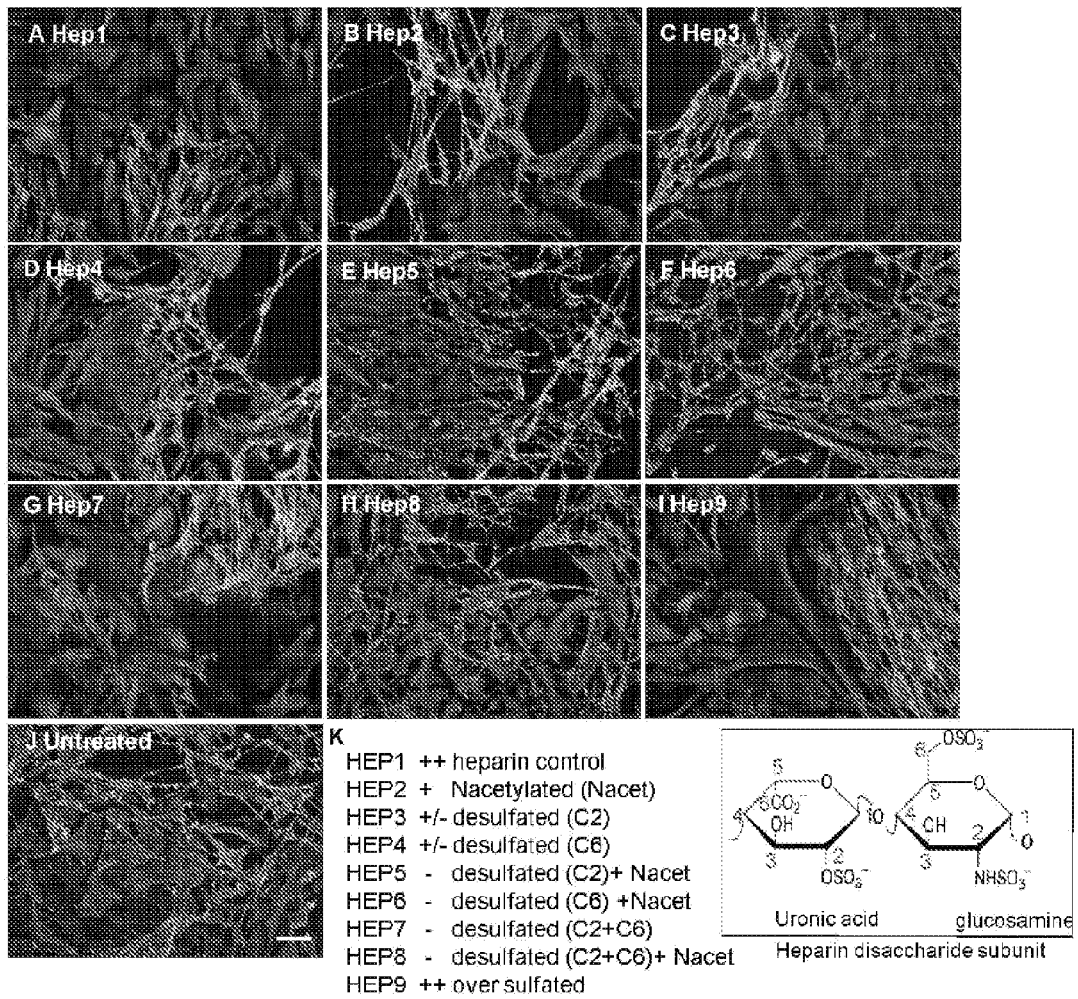
FIG. 3. HS sulfation is critical for boundary formation. Confrontation assays of OECs and astrocytes were carried out in the presence of 10 µg/ml modified heparins (A-J). The disaccharide structures of the heparins are indicated. After 2 days of treatment, cells were fixed and stained for GFAP (red) and $p75_{NTR}$ (green). Assays were scored using a graded scoring system to assess the ability of each modified heparin to promote boundary formation, i.e., mingling (−), partial boundary (+/−) or complete boundary (++) (K). Control heparin effect was scored as ++. Modified heparins with the highest levels of sulfation (Hep1, Hep2, Hep3, Hep4 and Hep9) induced boundaries between OECs and astrocytes, whereas those with lower levels of sulfation (Hep5, Hep6, Hep7 and Hep8) did not. The images are representative of at least 3 independent experiments. Scale bar 50 m.

In order to establish the effects of sulfation pattern on the inductive activity of HS, a panel of structurally defined, chemically modified (selectively desulphated) heparins were used to investigate the structural specificity of HS activity on boundary formation. After treatment with modified heparins (10 µg/ml) for 2 days, confrontation assays were stained for $p75^{NTR}$ and GFAP to visualise OECs and astrocytes, respectively. Results indicated that the most highly sulphated heparins (normal heparin (Hep1) or oversulphated heparin (Hep 9)) induced the strongest boundaries between OECs and astrocytes (FIG. 3 A, I), whilst lower sulphated heparin variants allowed OECs and astrocytes to mingle (FIG. 3 E-H). Interestingly, boundary formation was particularly dependent on O-sulfation, since N-acetylated heparin (in which N-sulfates are replaced with N-acetyl groups) induced significant boundary formation (Hep 2, FIG. 3 B), whereas either de-2-O-sulphated or de-6-O-sulphated heparins demonstrated lower boundary forming activity (Hep 3 and Hep 4, FIG. 3 C, D).

SCs Secrete More Highly Sulfated HS than OECs

Since it has been have shown that HS in SCM plays an active role in boundary formation, the structure of HS synthesised by SCs and OECs and shed into their surrounding environment was directly analysed. The disaccharide composition of SCM and OCM HS was, therefore, analysed via separation by strong anion exchange (SAX)-HPLC (FIG. 4A, B) and the relative abundance of each of the eight standard HS disaccharides were calculated as a percentage of total HS (FIG. 4C). SCM contains approximately two fold more HS than OCM, and in addition, SCM HS is more highly sulfated, with an average of 1.02 sulfates per disaccharide, compared to 0.75 sulfates per disaccharide in OCM HS (FIG. 4D). SCM HS consists of a higher proportion of di and tri-sulfated disaccharides (disaccharides 4, 5, 8 and 6) compared to OCM HS, and also a higher proportion of the singly 6-O-sulfated disaccharide (disaccharide 2). OCM HS, in contrast, contains a higher proportion of the unsulfated disaccharide (disaccharide 1). The proportion of singly N-sulfated (disaccharide 3) and singly 2-O-sulfated (disaccharide 7) disaccharides are similar in HS from both conditioned media.

SCs and OECs Express Different Levels of HS Biosynthetic Enzymes

Figure 5:
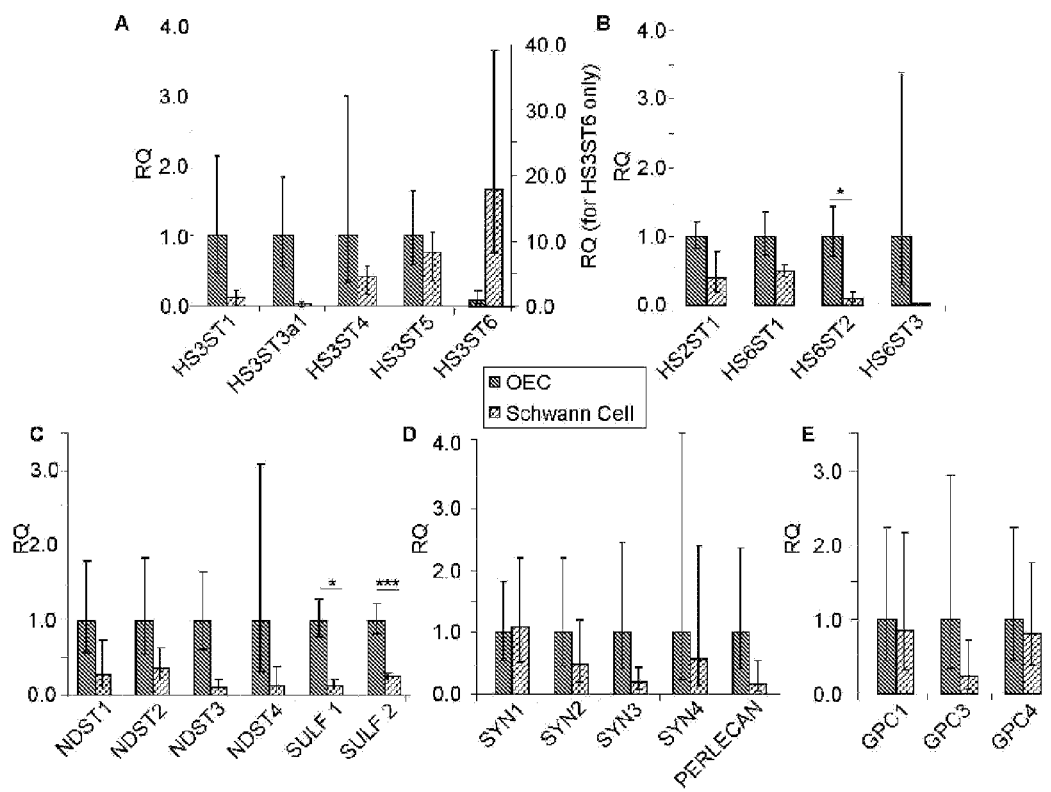
FIG. 5. Expression profile of HS biosynthetic enzymes and HSPGs in OECs and SCs. Using qRT-PCR, the expression of HS biosynthetic enzymes and HSPG core proteins by OECs and SCs were compared. Data are represented as relative quantification (RQ) of HS biosynthetic enzymes (A-C) and HSPGs (D-E) in SCs, normalised to the expression in OECs. HS6ST2, Sulf1 and Sulf 2 were more highly expressed by OECs. HS3ST6 was expressed uniquely by SCs, whereas HS6ST3 and HS3ST3a1 were expressed uniquely by OECs. HS3ST2, GPC2 and GPC5 were not expressed by either cell type. Error bars indicate ±SEM. * p<0.05, *** p<0.001 versus control.

To determine if differences in the expression of HS biosynthetic enzymes could account for the higher sulfation of SCM HS, quantitative PCR was carried out using cDNA generated from monocultures of OECs and SCs. Whilst there appeared to be a trend towards differences in expression of several enzymes by SCs compared to OECs, these were not significant due to variability in biological replicates. For example, there were no significant differences in the expression of N-deacetylase/N-sulfotransferase (NDST1-4) enzymes or many of the sulfotransferase enzymes. However, HS6-O-sulfotransferase 2 (HS6ST2) was expressed at a significantly higher level by OECs compared to SCs (FIG. 5B). In addition, HS6-O sulfotransferase 3 (HS6ST3) and HS3-O-sulfotransferase 3a1 (HS3ST3a1) were found to be uniquely expressed by OECs and HS3-O-sulfotransferase 6 (HS3ST6) was uniquely expressed by SCs (FIG. 5A). Interestingly, OECs express significantly higher levels of HS6-O-sulfatase enzymes compared to SCs (Sulf 1 and Sulf 2; 8-fold and 4-fold respectively) (FIG. 5C), which would be expected to reduce 6-O-sulfation of OECHS. These differences in HS biosynthetic and modification enzymes provide a potential explanation for the structural differences in HS synthesised and secreted by the two glial cell types. SCs and OECs express similar levels of the most common HSPG core proteins (FIG. 5D-E).

Reduction of Sulf 1 and Sulf 2 Expression in OECs Using RNAi Promotes Boundary Formation with Astrocytes Consistent with increased levels of 6-O-sulphated HS in SCDM, qPCR data indicated that SCs express lower levels of Sulf 1 and Sulf 2 6-O-endosulfatase enzymes compared to OECs. To determine if this was important for the ability of SCs to induce a boundary with astrocytes, OECs were transfected with siRNA targeted to Sulf 1 and Sulf 2 to see if the reduction in Sulf activity converted them to a more SC-like phenotype in confrontation assays. Prior to the addition of astrocytes, OECs were transfected with siRNA for 72 hours and the reduction of Sulf 1 and Sulf2 mRNA was confirmed by qPCR (~73% and ~63% knockdown respectively). Once the cells had met in confrontation assays, the numbers of OECs mingling with astrocytes across a 300 µm line were counted. Significantly less Sulf siRNA-treated OECs crossed into the astrocyte monolayer than control siRNA-treated OECs (4.6±1.3 Sulf siRNA cells compared with 15±1.8 control SiRNA OECs. p<0.01) and a clear boundary was observed, whereas control OECs and astrocytes mingled freely (FIG. 6A-B). This suggests that an increase in HS 6-O-sulfation in OECs, via reduced Sulf expression, induces SC-like behaviour. The complimentary experiment to over-express Sulf 1 and Sulf 2 in SCs to determine if they adopted an OEC-like phenotype was attempted using pcDNA3.1/Myc-His(−)-MSulf-1 and pcDNA3.1/Myc-His(−)-MSulf-2[36]. However, it was not possible to gain conclusive data using transfected cells in confrontation assays due to the low transfection efficiency of primary SCs (<3%, data not shown), which has also been reported by others[55]. An alternative experiment based on the hypothesis that it may be possible to interfere competitively with endogenous highly sulphated HS in SC/astrocyte boundaries using an excess of low sulphated modified heparins that do not promote boundary formation (eg., Hep 6, 7 and 8 in FIG. 3). Confrontation assays of SC and astrocytes treated with each of the low sulphated modified heparins demonstrated significantly increased cell mingling (FIG. 7), confirming the hypothesis that these HS mimetics can inhibit boundary formation, presumably by competing for endogenous FGF ligands and reducing activation of astrocyte FGFR.

Inhibition of FGF1 or FGF9 Disrupts SC Boundary Formation with Astrocytes

Figure 8:
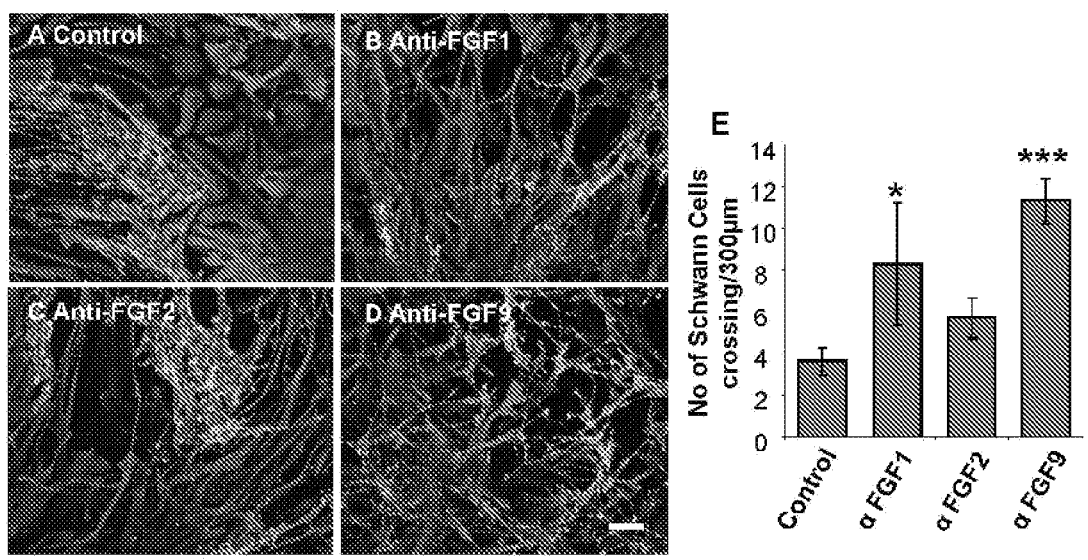
FIG. 8. Neutralisation of FGF1 and FGF9 disrupts boundary formation between SCs and astrocytes. SC and astrocyte confrontation assays were treated with 1 g/ml FGF1 (B), FGF2 (C) or FGF9 (D) blocking antibodies for 2 days after the cell populations had met. Cells were fixed and stained for GFAP (red) and p75$_{NTR}$(green) and the numbers of SCs mingling with astrocytes across a 300 m line were counted (E). Neutralisation of FGF1 and FGF9, but not FGF2, resulted in an increase in mingling between SCs and astrocytes compared to control cultures (A). Error bars indicate ±SEM. Scale bar 50 m. * p<0.05, *** p<0.001 versus control.

It has long been established that HS is required for the proper function of FGF by supporting the binding of all members of the FGF family to their cognate FGFRs[38,44,51]. The differential sulfation of HS is also known to regulate FGF activity[28,41]. Previously, it has been shown that FGFR inhibition disrupts SCM-induced boundary formation in OEC/astrocyte cultures[11], suggesting that a target of HS regulation of boundary formation is a member of the FGF family. We, therefore, investigated the role of particular FGF ligands in boundary formation. The FGFR inhibitor used in the aforementioned study (SU5402) was previously thought to specifically inhibit FGFR1, however, it has also been shown to effectively inhibit FGFR3[27,39]. Astrocytes, but not OECs or SCs, express FGFR3-IIIb[11], suggesting that the response observed with the SU5402 inhibitor in confrontation assays may be due to inhibition of this receptor on astrocytes. FGF1 and FGF9 are the only known ligands for FGFR3-IIIb[21,29,45], therefore, the effect of blocking FGF1 or FGF9 using neutralising antibodies was investigated. Since FGFR3-IIIb does not bind FGF2[21], a neutralising antibody against FGF2 was used as a negative control. Inhibition of FGF1 or FGF9 in SC/astrocyte confrontation assays resulted in reduced boundary formation and increased cell mingling, whereas inhibition of FGF2 had no effect (FIG. 8).

DISCUSSION

Glial cell transplantation is a promising strategy for the repair of damaged CNS following injury or disease, with OECs and SCs as potential candidates. OECs may be the preferred candidate due to their ability to evoke less of a stress response in astrocytes[10,11,23]. However, since SCs often invade the CNS after injury when the blood brain barrier is breached[14], it is important to understand the mechanisms by which they induce an astrocytic stress response, in order to devise strategies to prevent it. Previously, it has been shown that addition of heparin to OEC/astrocyte co-cultures induces boundary formation and removal of endogenous HS or inhibition of HS sulfation in SC/astrocyte cultures results in cell mingling[11]. In this study, we have demonstrated that the sulfation of HS synthesised by SCs and OECs is a crucial feature of their molecular phenotype influencing their activity on contacting astrocytes. The ability of HS to induce a boundary between SCs and astrocytes is shown to be dependent upon the level and pattern of HS sulfation, is modulated by the extracellular sulfatases, Sulf 1 and Sulf 2, and is likely to be mediated via FGF1 and/or FGF9 activation of astrocyte FGFR3-IIIb signalling. This information provides new targets for the development of strategies to enhance post-transplantation integration of SCs into CNS tissue.

Figure 4:
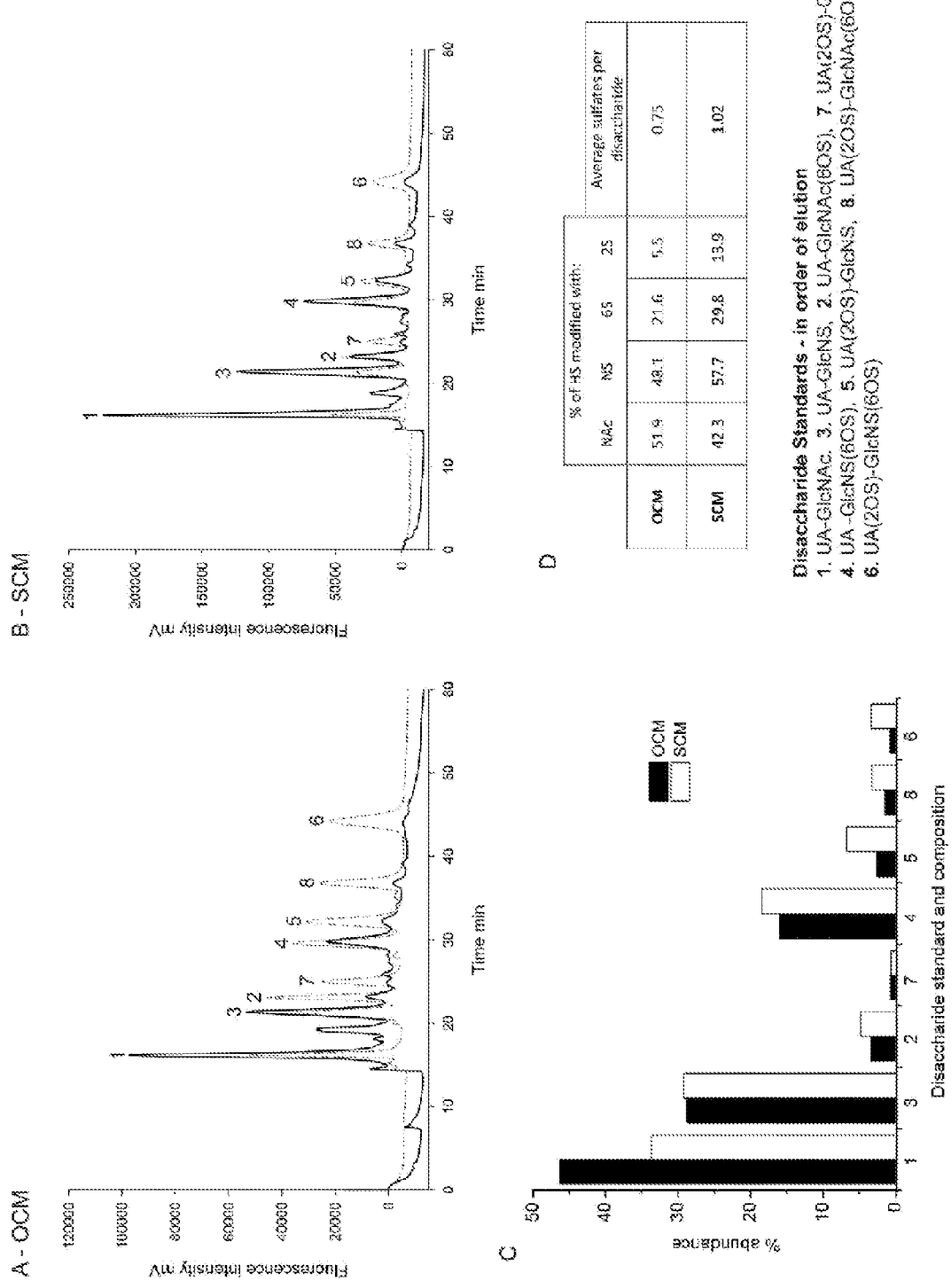
FIG. 4. SAX-HPLC analysis of fluorescently labelled HS disaccharides purified from OCM and SCM indicate that SCs and OECs secrete distinct HS structures. HS purified from OCM (A) and SCM (B) was digested with heparinase enzymes to generate HS disaccharides, which were fluorescently labelled with BODIPY and separated by SAX-HPLC over a 45 minute, 0-1.5 M NaCl gradient, (A and B, black lines). HS disaccharide standards were separated over the same gradient as a reference guide (A and B, dashed lines). Relative abundances of the eight HS standard disaccharides in each conditioned medium sample were calculated as a percentage of total HS (C). A summary table detailing the composition of OCM HS and SCM HS is also presented (D). SCM HS was found to be more highly sulphated than OCM HS, with an average of 1.02 sulfates per disaccharide compared to 0.75 sulfates per disaccharide in OCM HS (D). SCM HS contained a higher proportion of di- and tri-sulphated disaccharides (disaccharides 4, 5, 8 and 6) and the singly 6-O-sulphated disaccharide (disaccharide 2) compared to OCM HS (C), which contained a higher proportion of the unsulphated disaccharide (disaccharide 1) (C, D). (UA) uronic acid, (GlcN) glucosamine, (NAc)N-acetyl, (NS)N-sulfate, (6OS) 6-O-sulfate, (2OS) 2-O-sulfate.

Using chemically modified heparins, which are model HS compounds with different levels of sulfation, it was possible to correlate HS sulfation with the extent of mingling/boundary formation induced in OEC/astrocyte confrontation assays. The more highly sulphated structures induced a stronger OEC:astrocyte boundary compared to the less sulphated structures, with a particular dependence on O-sulfation (FIG. 3). In support of this, HS isolated from SCM, which induces a boundary in OEC/astrocyte cultures, was 27% more sulphated than OCM HS, with a particular enhancement of 6-O-sulphated and 2-O-sulphated disaccharides (FIG. 4). Differences in the structure of HS synthesised by the glial cells will reflect a difference in biological activity and function, since HS:protein interactions are mediated by specific HS structures.

Figure 6:
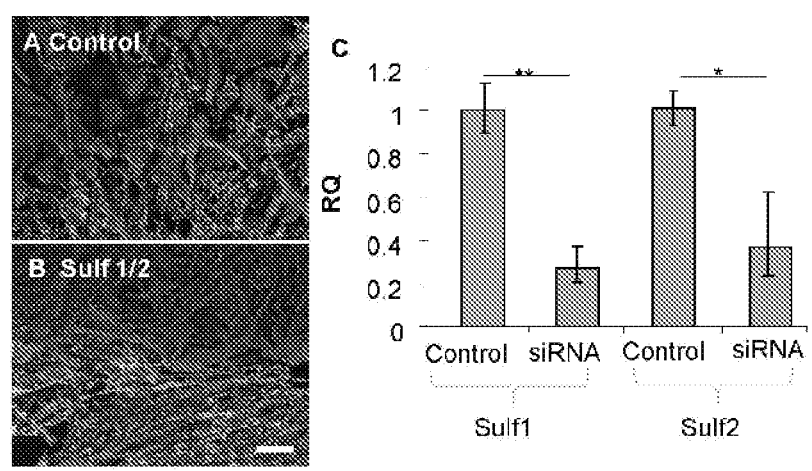
FIG. 6. Knockdown of Sulf expression in OECs promotes boundary formation with astrocytes. Confrontation assays were performed using astrocytes and either OECs transfected with nontargeting control siRNA (A) or OECs transfected with siRNAs targeted to Sulf 1 and Sulf 2 (B). After 2 days, cells were fixed and stained for GFAP (red) and p75$_{NTR}$ (green). OECs depleted of Sulf 1 and Sulf 2 expression formed a boundary on contact with astrocytes, whereas astrocytes and control treated OECs mingled. The extent of gene knockdown was assessed by qPCR using RNA purified from siRNA treated cells and Sulf 1 and Sulf 2 specific primers and was found to be 70% and 63% reduced respectively (C). Error bars indicate ±SEM. Scale bar 50 m. *p<0.05, ** p<0.01 versus control.
Figure 7:
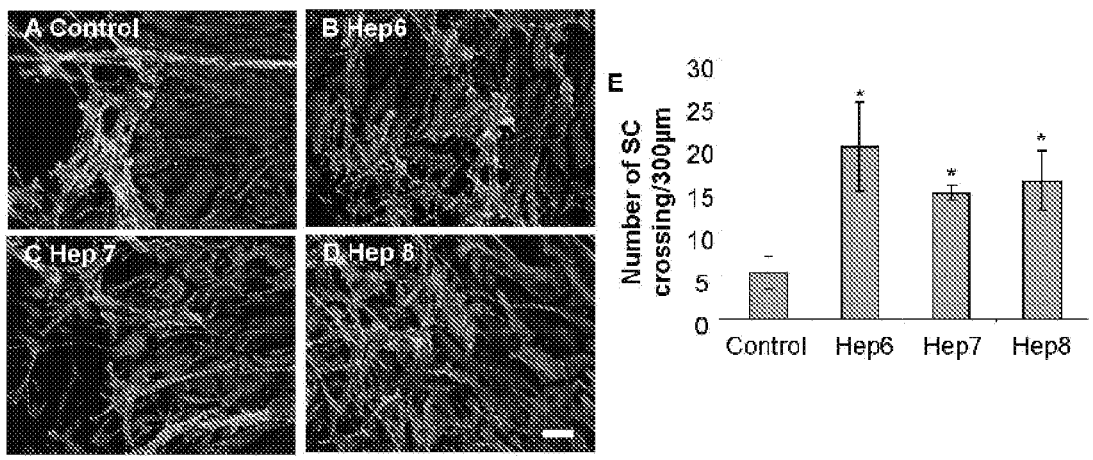
FIG. 7. Interference of endogenous SC HS function using HS mimetics to inhibit boundary formation. Confrontation assays of SCs and astrocytes were carried out in the absence (A) or presence (B-D) of 10 f g/ml selectively chemically modified heparins (Hep 6, 7, 8; see FIG. 3 for structural details) with low levels of sulfation. After 2 days of treatment, cells were fixed and stained for GFAP (red) and p75$_{NTR}$(green) and the numbers of SCs mingling with astrocytes across a 300 m line were counted (E). The addition of low sulphated modified heparins (HSmimetics) to confrontation assays resulted in an increased number of SCs mingling with astrocytes (B-D) compared to in control cultures (A). Error bars indicate ±SEM. Scale bar 50 m. * p<0.05 versus control.

Further evidence for a role of Sulf modified HS in boundary formation was obtained by siRNA mediated knock down of Sulf 1 and Sulf 2 expression in OECs (FIG. 6). Cell behaviour was altered dramatically, resulting in a phenotypic switch towards a SC-like response on contact with astrocytes and formation of a boundary. This strongly suggests that Sulf enzymes expressed by OECs play a vital role in modifying HS fine structure to determine their biological function.

Removal of specific 6-O-sulfates from HS by Sulf enzymes will affect HS:protein interactions and, therefore, subsequent signalling pathways involved in boundary formation, allowing the cells to mingle with astrocytes. Reduction in Sulf enzyme expression diminishes this extracellular control of HS 6-O-sulfation, resulting in the synthesis of OEC HS that is more highly sulphated and SC-like and, thus, able to activate the signalling cascades that underlie boundary formation. Conversely, by saturating SC/astrocyte confrontation assays with low sulphated HS mimetics, we demonstrated that it is possible to inhibit SC-induced boundary formation (FIG. 7), potentially by out-competing SC HS for the activating FGF ligands. This is consistent with the notion that highly sulphated HS produced by SCs is essential for activation of boundary forming signalling pathways.

Figure 2:
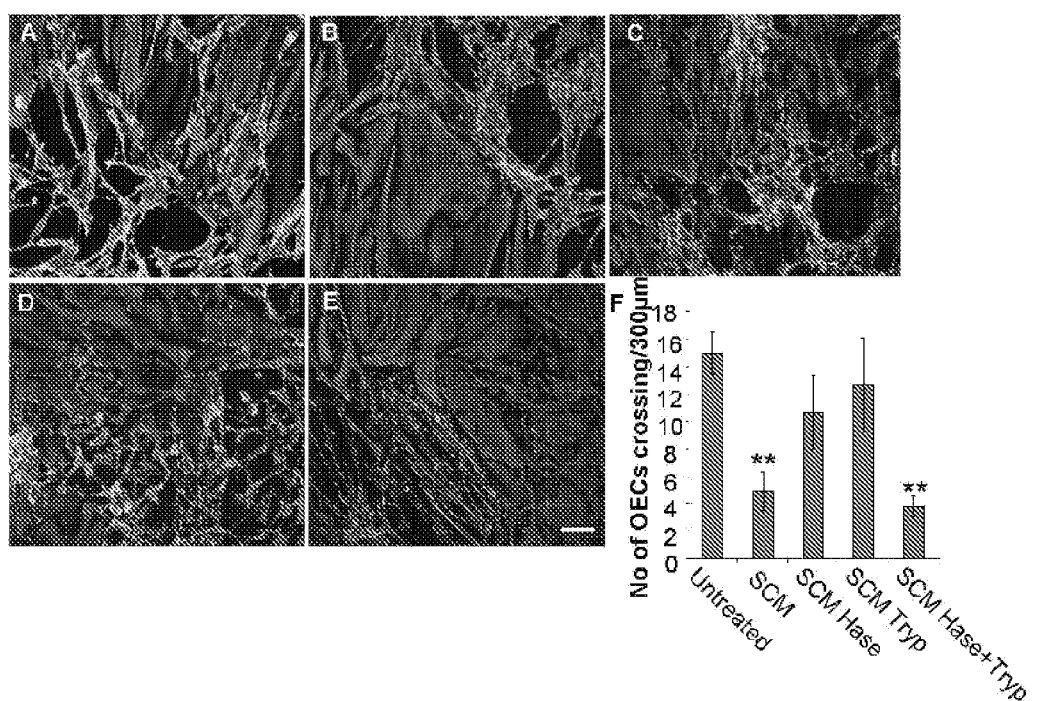
FIG. 2. Both HS and protein components of SCM are required for boundary formation. Confrontation assays of OECs and astrocytes were carried out in the presence of; normal medium/untreated (A); SCM (B); heparinase treated SCM (C); trypsin treated SCM (D); 1:1 combination of heparinase treated and trypsin treated SCM (E). After 2 days of treatment, cells were fixed and stained for GFAP (red) and $p75_{NTR}$ (green). The number of cells mingling with astrocytes was counted across a 300 ⌠m line (F). Heparinase or trypsin treated SCM did not induce boundary formation when added to assays individually, however, when combined, a boundary formed, suggesting that both an HS and protein component are required for activity. Error bars indicate ±SEM. Scale bar 50 m. ** $p<0.01$ versus control.
Figure 9:
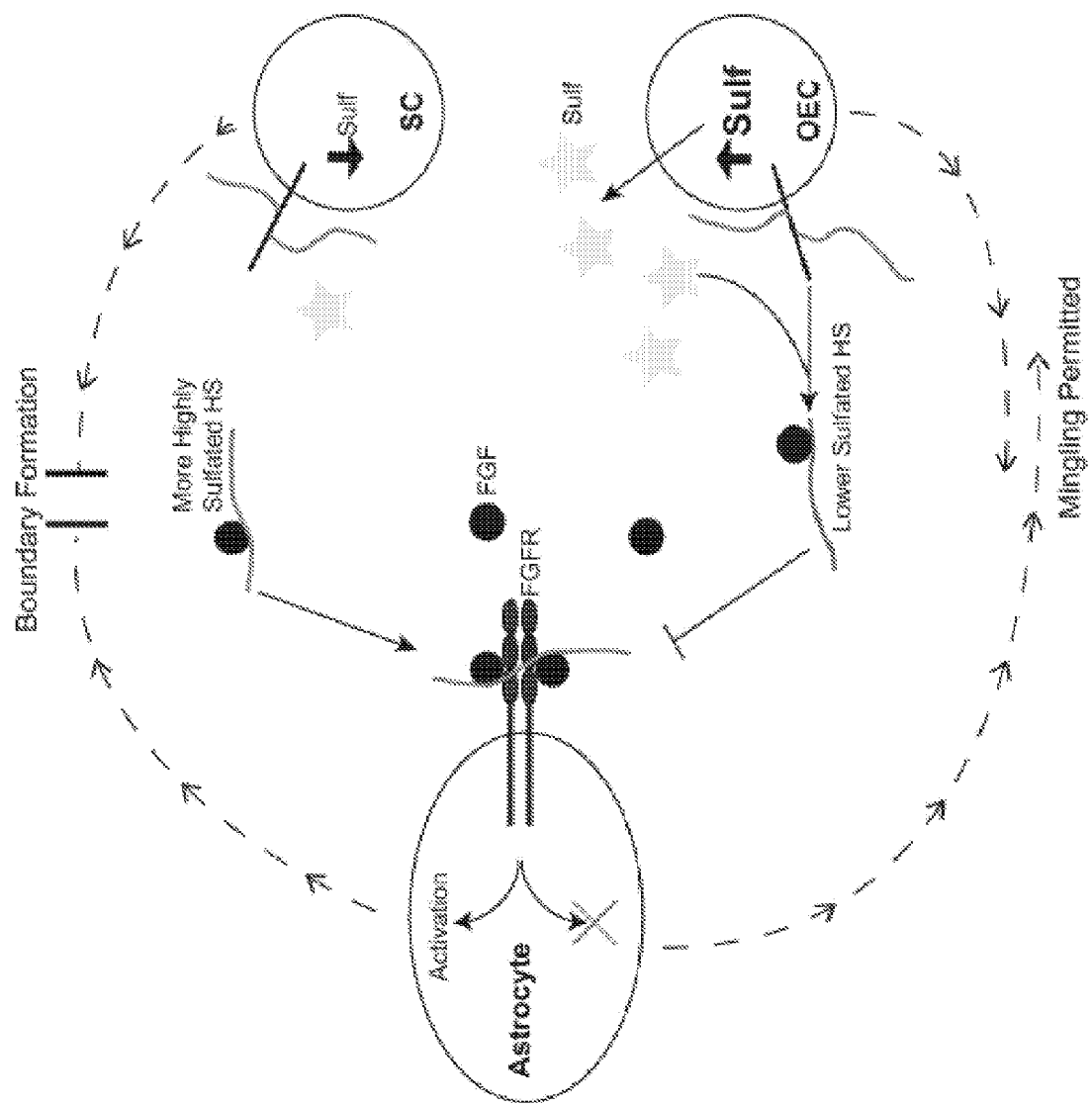
FIG. 9. A model of HS function in SC/astrocyte boundary formation. SCs secrete a highly sulphated HS (green chains), due to low level expression of Sulf enzymes. This HS promotes FGF1 and/or FGF9 ligand (black circles) binding to and/or activation of FGFR3-IIIb receptor (blue) on astrocytes, activating intracellular signalling pathways and resulting in altered cell phenotype (blocking of mingling) and the formation of a boundary. OECs secrete a lower sulphated HS (red chains), due to higher expression of Sulf enzymes (yellow stars), which selectively remove 6-O-sulfates. These lower sulphated HS chains cannot promote FGF1 or FGF9 binding to and/or activation of FGFR3-IIIb on astrocytes, and so fail to activate the required signalling pathways that lead to boundary formation, thus, enabling OECs to mingle with astrocytes.

In addition to the requirement for an HS component in SCM to induce an OEC:astrocyte boundary, a protein factor in SCM is also needed, since treatment of SCM with trypsin abolishes SCM activity. Reconstitution of separately heparinase- or trypsin-treated SCM samples restores SCM activity, further demonstrating the necessity of both an HS and protein component for activity (FIG. 2). Previously, FGFs were implicated, since inhibition of FGFR in SC:astrocyte cultures and OEC:astrocyte cultures treated with SCM reduced astrocyte hypertrophy and boundary formation[11]. Notably, in the same study, the expression of FGFRs in SCs, OECs and cortical astrocytes were analysed, and FGFR3-IIIb was found to be uniquely expressed by astrocytes. FGF1 and FGF9 are the only known ligands for FGFR3-IIIb[21,29,45]. In the current study, inhibition of FGF1 and FGF9 activity in confrontation assays resulted in mingling of SCs and astrocytes, whilst inhibition of FGF2 had no effect (FIG. 8). Interestingly, FGF9, also known as glial activating factor[45], has previously been reported to stimulate GFAP expression in human glioma cells[35], a process that also occurs during boundary formation[10]. This data is consistent with the notion that signalling through FGFR3-IIIb is crucial for astrocyte boundary formation. FIG. 9 presents a model in which FGF1 and/or FGF9 can only bind to and activate FGFR3-IIIb if a more highly sulphated HS is present in the conditioned medium via direct secretion of an extracellular matrix HSPG such as perlecan or by shedding of cell surface HSPGs such as syndecans[19,43] or glypicans[32,47]. This leads to activation of astrocytes and subsequent boundary formation with SCs.

Lower sulphated HS synthesised by OECs, formed as a result of higher Sulf expression, cannot support FGF induced FGFR3-IIIb signalling, resulting in mingling between astrocytes and OECs.

The findings of this study demonstrate the prospect for significant advancements in combinatorial approaches for CNS repair after injury and in neurodegenerative diseases in which astrocytes become reactive. For example, transiently modifying HS structure by modulating the expression of HS sulfatase enzymes in transplanted SCs to enhance engraftment is a viable option.

It may also be possible to manipulate HS sulfation levels at the CNS injury site, possibly by direct addition of Sulf enzymes into the lesion, or alternatively, to interfere with endogenous HS activities using HS mimetics.

REFERENCES

1. Sofroniew M, Vinters H V (2010). Acta Neuropathol 119:7-35.
2. Eng L et al., (1971) Brain Res 8:351-4.
3. Maragakis N J, Rothstein J D (2006) Nat Clin Pract Neurol 2:679-89.
4. Eddleston M, Mucke L (1993) Neurosci 54:15-36.
5. Liberrto et al., (2004) J Neurochem 89:1092-100.
6. Nash B, et al., (2010) Astrocyte phenotypes and their relationship to myelination. J Anat 219:44-52.
7. Barnett S C, Riddell J S. (2007) Nat Clin Pract Neurol 3:152-61.
8. Reier P J (2004) NeuroRx 1:424-51.
9. Franklin R J et al., (2008) Nat Rev Neurosci 9:839-55.
10. Lakatos A et al., (2000) Glia 32:214-25.
11. Santos-Silva A et al., (2007) J Neurosci 27:7154-67.
12. Fairless R et al., (2005) Mol Cell Neurosci. 28:253-63.
13. Franklin R J M, Blakemore W F (1993) Int J Dev Neurosci 11:641-49.
14. Bruce et al., (2000) J Neurotrauma 17:781-8.
15. Yates E A et al., (2004) J Med Chem 47:277-280.
16. Patey S J et al., (2006) J Med Chem 49, 6129-6132.
17. Guimond S E et al., (2006) Macromol Biosci. 6; 681-686.
18. Alexander C L et al., (2002) Glia 37:349-364.
19. Asundi V K et al., (2003) J Neurosci Res 73:593-602.
20. Brockes J P et al., (1979) Brain Res 165:105-118.
21. Chellaiah A T et al., (1994) J Biol Chem 269:11620-11627.
22. Chuah M I, West A K (2002) Microsc Res Tech 58:216-227.
23. Fairless R, Barnett S C (2005) Int J Biochem Cell Biol 37:693-699.
24. Fawcett J W, Asher R A (1999) Brain Res Bull 49:377-391.
25. Franklin R J, Barnett S C (2000) Neuron 28:15-18.
26. Franssen E H et al., (2007) Brain Res Rev 56:236-258.
27. Grand E K et al., (2004) Leukemia 18:962-966.
28. Guimond S et al., (1993) J Biol Chem 268:23906-23914.
29. Hecht D et al., (1995) Growth Factors 12:223-233.
30. Higginson J R, Barnett S C (2010) Exp Neurol 229:2-9.
31. Irie A et al., (2002) Development 129:61-70.
32. Kreuger J et al., (2004) Dev Cell 7:503-512.
33. Lakatos A et al., (2003) Exp Neurol 184:237-246.
34. Li Y et al., (2005) Glia 52:245-251.
35. Miyagi N et al., (1999) Oncol Rep 6:87-92.
36. Morimoto-Tomita M et al., (2002) J Biol Chem 277: 49175-49185.
37. Noble M, Murray K (1984) EMBO J 3:2243-2247.
38. Omitz D M et al., (1992) Mol Cell Biol 12:240-247.
39. Paterson J L et al., (2004) Br J Haematol 124:595-603.
40. Pekny M, Nilsson M (2005) Glia 50:427-434.
41. Pye D A et al., (1998) J Biol Chem 273:22936-22942.
42. Raisman G (1985) Neuroscience 14:237-254.
43. Ramani V C et al., (2012) J Biol Chem 287:9952-61.
44. Rapraeger A C et al., (1991) Science 252:1705-1708.
45. Santos-Ocampo S et al., (1996) J Biol Chem 271:1726-1731.
46. Silver J, Miller J H (2004) Nat Rev Neurosci 5:146-156.
47. Traister A et al., (2008) Biochem J 410:503-511.
48. Wilby M J et al., (1999) Mol Cell Neurosci 14:66-84.
49. Yan Q, Johnson E M, Jr. (1988) J Neurosci 8:3481-3498.
50. Yates E A et al., (1996) Carbohydr Res 294:15-27.
51. Yayon A et al., (1991) Cell 64:841-848.
52. Skidmore M A et al., (2009) Methods Mol Biol 534: 157-169.
53. Skidmore M A et al., (2010) Nat Protoc 5:1983-1992.
54. Skidmore M A et al., (2006) J Chromatogr A 1135:52-56.
55. Kraus A, et al., Neuron Glia Biol 6:225-230.

The invention claimed is:

1. A method of transplanting cells into central nervous system (CNS) tissue in a patient in need of such treatment, said method comprising administering said cells into said CNS tissue and treating said patient with a therapeutically effective amount of an agent selected from the group consisting of:
(i) a heparin derivative which is:
substantially 6-O desulphated and 2-N desulphated;
substantially 2-O desulphated and 6-O desulphated; and/or
substantially 2-O desulphated, 6-O desulphated and 2-N desulphated,
wherein a heparin derivative that is substantially 6-O desulphated has 50% to 100% of the 6-O atoms of glucosamine moieties desulphated; and
(ii) a selective FGF-1 and/or FGF-9 inhibitor, wherein the inhibitor is an antibody;
or a pharmaceutically acceptable salt or solvate of said agent, either prior to, during or following cell transplantation into said CNS tissue.

2. The method according to claim 1, wherein said agent is the heparin derivative.

3. The method according to claim 1, wherein the heparin derivative exhibits less than 5% of the Anti-Factor Xa activity of unmodified porcine intestinal mucosal heparin.

4. The method according to claim 1, wherein 50 to 100% of the 6-O atoms of the glucosamine moieties of the heparin derivative are substituted with hydrogen.

5. The method according to claim 1, wherein the heparin derivative has the general structural formula I shown below:

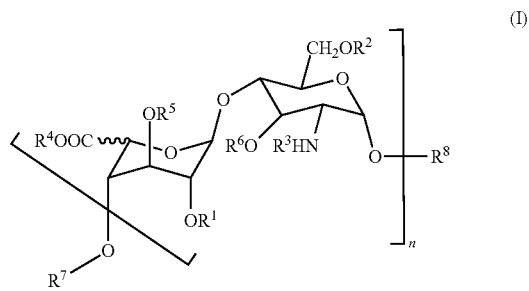

wherein:
$R^1$ and $R^2$ are selected from hydrogen or sulphate;
n is 1 to 30;
$R^3$ is selected from sulphate, hydrogen, substituted or unsubstituted alkyl, substituted or unsubstituted aryl, substituted or unsubstituted acyl, substituted or unsubstituted amido and phosphate;
$R^4$, $R^5$ and $R^6$ are each separately selected from the group consisting of hydrogen, sulphate, phosphate, substituted or unsubstituted (1-6C)alkyl, substituted or unsubstituted (1-6C)alkoxy, substituted or unsubstituted aryl, substituted or unsubstituted aryloxy, substituted or unsubstituted acyl, and substituted or unsubstituted amido; and $R^7$ and $R^8$ are each separately selected from the group consisting of hydrogen, substituted or unsubstituted alkyl, substituted or unsubstituted aryl, substituted or unsubstituted acyl, a terminal monosaccharide group, a terminal disaccharide group and/or fragments or derivatives thereof;
or a pharmaceutically acceptable salt or solvate thereof; with the proviso that:
(i) between 50% to 100% of the $R^2$ groups present are hydrogen and between 50% to 100% of the $R^3$ groups present are hydrogen or a substituent group other than sulphate;
(ii) between 50% to 100% of the $R^1$ and $R^2$ groups present are hydrogen; or
between 50% to 100% of the $R^1$ and $R^2$ groups present are hydrogen; and between 50% to 100% of the $R^3$ groups present are hydrogen or a substituent group other than sulphate.

6. The method according to claim 5, wherein in the heparin derivative of formula I:
(i) between 80-100% of all $R^2$ groups present are hydrogen and 80-100% of the $R^3$ groups present are hydrogen or a substituent group other than sulphate (e.g. acetyl) and greater than 75% of the $R^1$ groups are sulphate;
(ii) between 80-100% of all $R^2$ and $R^1$ groups present are hydrogen and greater than 75% of the $R^3$ groups are sulphate; and/or
(iii) between 80-100% of all $R^2$ and $R^1$ groups present are hydrogen and 80-100% of the $R^3$ groups present are hydrogen or a substituent group other than sulphate.

7. The method according to claim 5, wherein $R^4$, $R^5$ and $R^6$ are each independently selected from hydrogen or sulphate.

8. The method according to claim 1, wherein the heparin derivative has an average molecular weight of from 500 Da to 30 kDa.

9. The method according to claim 1, wherein the degree of polymerisation of the heparin derivative ranges from 2 monomer units to 60 monomer units.

10. The method according to claim 1, wherein the cells are a glial cells.

11. The method according to claim 1, wherein the cells are selected from Schwann cells and olfactory ensheathing cells.

12. The method according to claim 1, wherein a heparin derivative that is substantially 6-O desulphated has 75% to 100% of the 6-0 atoms of glucosamine moieties desulphated.

13. The method according to claim 1, wherein a heparin derivative that is substantially 6-O desulphated has 90% to 100% of the 6-0 atoms of glucosamine moieties desulphated.

* * * * *